US005792458A

United States Patent [19]

Johnson et al.

[11] Patent Number: 5,792,458

[45] Date of Patent: Aug. 11, 1998

[54] MUTANT DIPHTHERIA TOXIN CONJUGATES

[75] Inventors: Virginia G. Johnson, College Park, Md.; Larry Greenfield, Emeryville, Calif.; Richard J. Youle, Garrett Park, Md.; Walter Laird, Pinole, Calif.

[73] Assignees: The United States of America as represented by the Department of Health and Human Services, Washington, D.C.; Cetus Corporation, Emeryville, Calif.

[21] Appl. No.: 323,591

[22] Filed: Oct. 17, 1994

Related U.S. Application Data

[60] Continuation of Ser. No. 934,250, Aug. 25, 1992, abandoned, which is a division of Ser. No. 301,376, Jan. 25, 1989, Pat. No. 5,208,021, which is a division of Ser. No. 236,225, Aug. 25, 1988, abandoned, which is a continuation-in-part of Ser. No. 105,172, Oct. 5, 1987, abandoned.

[51] Int. Cl.$^6$ .......................... C12N 9/00; A61K 39/44; A61K 38/16; A61K 39/395

[52] U.S. Cl. .......................... 424/183.1; 424/155.1; 424/174.1; 424/94.1; 424/832; 514/12; 530/350; 530/387.7; 530/391.7

[58] Field of Search .......................... 424/183.1, 832, 424/194.1, 195.11, 143.1, 154.1, 85; 514/8, 12, 21; 530/391.7, 394, 380, 388.1, 388.2, 388.22, 387.7, 388.8, 363, 388.75, 588

[56] References Cited

U.S. PATENT DOCUMENTS

| | | | |
|---|---|---|---|
| 4,520,226 | 5/1985 | Neville et al. | 424/85 |
| 4,545,985 | 10/1985 | Pastan et al. | 424/85 |
| 4,675,382 | 6/1987 | Murphy | 530/350 |
| 4,830,962 | 5/1989 | Gelford et al. | 435/69.1 |
| 4,894,443 | 1/1990 | Greenfield et al. | 530/388 |
| 4,956,453 | 9/1990 | Bjorn et al. | 530/387.1 |
| 4,981,979 | 1/1991 | Sivam | 530/389 |
| 5,045,451 | 9/1991 | Uhr | 435/7.23 |
| 5,066,490 | 11/1991 | Neville et al. | 424/85.91 |
| 5,154,924 | 10/1992 | Friden | 424/85.91 |
| 5,169,956 | 12/1992 | Neville et al. | 424/85.91 |
| 5,182,107 | 1/1993 | Fridan | 424/85.91 |
| 5,208,021 | 5/1993 | Johnson et al. | 424/85.91 |
| 5,352,447 | 10/1994 | Johnson et al. | 424/183.1 |

OTHER PUBLICATIONS

Trowbridge et al (1981) Nature 294: 171–173.
Youle et al (1980) Proc. Natl. Acad. Sci. USA 77: 5483–5486.
Domingo et al (1985) Methods Enzymol. 112: 238–247.
Youle et al (1986 Jan.) J. Immunol. 136(1): 93–98.
Laird et al, Journal of Virology, vol. 19, No. 1, pp. 220–227 (1976).
Annual Progress Report, U.S. Army Medical Research Institute of Infectious Diseases, pp. 95–96 (1981).
Zovickian et al, J. Neurosurg., vol. 68, pp. 767–774 (1988).
Neville, Jr. et al, The Journal of Biological Chemistry, vol. 264, No. 25, pp. 14653–14661 (1989).
Greenfield et al, Science, vol. 238, pp. 536–539 (1987).
Richard Youle et al., Proc. Natl. Acad. Sci. USA, vol. 76, No. 11, pp. 5559–5562 (1979).
Richard Youle et al., Cell, vol. 23, pp. 551–559 (1981).
Colombatti, M. et al. Journal of Biological Chemistry 261(7):3030–3035, Mar. 1986.
O'Keefe et al (1985) J. Biol. Chem. 260(2):932–937.
Zovickian et al (1987) J. Neurosurg. 66:850–861.
Goldstein et al (1986) Scientific America 255:74–83.
Bach et al (1993) Immunology Today 14:421–425.
Waldmann (1991) Science 252:1657–1662.
Jach (1994) Scientific American (Jul. issue):58–65.
Gregonadis et al (1993) Trends in Biotech 11:440–442.
Rott (1991) "Essential Immunology", Blackwell Scientific Publications Oxford, pp. 65–68 & 74.
Piedel et al (1990) Proc. Nat'l Acad. Sci. 87:5051–5055.
Sovza et al (1995) Proc. Natl. Acad. Sci. 92:959–963.
Largo et al (1988) Molec. Cell. Biol. 8(3):1247–1252.
Esworthy et al (1984) J. Biol. Chem. 259(18):11496–11504.
Morrison et al (1972) "Organic Chemistry," Allyer and Bacon, Inc., Boston, p. 6.
Johnson et al (1989) J. Neurosurg: 70:240–248.
Youle (1991) Semin. Cell Biol. 2: 39–45.
Youle et al (1988) In "Immunotoxins" (A.E. Frankel, ed.), Kluiver Academic Publications, pp. 113–119.
Youle et al, *The Journal of Immunology*, vol. 136, No. 1, pp. 93–98, Jan. 1986.
Akiyamas et al, *Cancer Research*, vol. 45, pp. 1005–1007, 1985.
Jeffries et al (1984) Nature 312: 162–163.
Akiyama et al, *Cancer Research*, vol. 45, pp. 1005–1007, 1985.
Seto et al, *Cancer Research*, vol. 42, pp. 5209–5215, Dec. 1982.

*Primary Examiner*—Toni R. Scheiner
*Assistant Examiner*—John Lucas
*Attorney, Agent, or Firm*—Klarquist Sparkman Campbell Leigh & Whinston

[57] ABSTRACT

A potent and specific immunotoxin is prepared by coupling an inactivated diphtheria toxin to a binding moiety such as a monoclonal antibody or transferrin. The immunotoxins are specific for human tumors and leukemias and are indistinguishable in cell toxicity from that of the native toxin linked to the binding domain without the toxicity to other cells. The immunotoxin is useful in treating graft versus host disease as well as selectively killing tumor cells, such as medulloblastoma and glioblastoma cells.

39 Claims, 9 Drawing Sheets

MUTANT DIPHTHERIA TOXIN CONJUGATES

This application is a continuation of application Ser. No. 07/934,250, filed Aug. 25, 1992 and now abandoned, which in turn was a division of Ser. No. 07/301,376, filed Jan. 25, 1989, now issued as U.S. Pat. No. 5,208,021, which in turn was a division of Ser. No. 07/236,225, filed Aug. 25, 1988, now abandoned, which in turn was a continuation-in-part of Ser. No. 07/105,172, filed Oct. 5, 1987, now abandoned.

FIELD OF THE INVENTION

The present invention relates to cancer chemotherapy, and, more particularly, to a reagent which selectively kills cancer cells and can be used to treat graft versus host disease.

BACKGROUND OF THE INVENTION

Current treatments utilizing surgery, radiation therapy, and systemic chemotherapy have done little to alter the natural outcome of many malignant tumors of the central nervous system.

The use of cytotoxic products in the treatment of cancer is well known. The difficulties associated with such treatment are also well known. Of these difficulties, the lack of cancer-specific cytotoxicity has received considerable attention, albeit resolution of these difficulties has met with marginal success. Cytotoxic products kill normal cells as well as cancer cells. Such non-specificity results in a number of undesirable side effects for patients undergoing cancer chemotherapy with cytotoxic products, including nausea, vomiting, diarrhea, hemorrhagic gastroenteritis, and hepatic and renal damage. Due to normal cell toxicity, the therapeutic dosage of cytotoxic products has been limited such that cancerous cells are not killed to a sufficient level that subsequently prevents or delays new cancerous growth.

Current approaches to cancer chemotherapy and other immunological therapies focus on the use of cell-specific antibodies bonded to toxins in order to kill specific populations of cancer cells. Immunotoxins (protein toxins chemically linked to tumor-specific monoclonal antibodies or other ligands) offer potential advantages over more conventional forms of treatment by having higher tumor specificity. Ideally, immunotoxins should discriminate to a high degree between target and non-target cells. The critical point, then, is the development of immunotoxins that are highly toxic for specific populations of cells.

Monoclonal antibodies linked to toxic proteins (immunotoxins) can selectively kill some tumor cells in vitro and in vivo. However, reagents that combine the full potency of the native toxins with the high degree of cell-type selectivity of monoclonal antibodies have not previously been designed.

Immunotoxins may be particularly efficacious for the treatment of neoplastic disease confined to compartments such as the peritoneum or intrathecal space. Direct delivery into the compartment avoids complications associated with systemic delivery and produces relatively high local concentrations, thereby achieving greater therapeutic effects. The cerebrospinal fluid compartment may be amenable to this type of compartmentalized immunotoxin treatment. Zovickian and Youle, *J Neurosurg*, in press, examined the therapeutic effect of a monoclonal antibody-ricin immunotoxin delivered directly into the CSF compartment in a guinea pig model of leptomeningeal neoplasia. The immunotoxin therapy extended survival, corresponding to a 2–5 log kill of tumor cells, without detectable toxicity.

Protein toxins used in the constructions of immunotoxins have an A and a B subunit. The A subunit catalyzes the inactivation of protein synthesis, resulting ultimately in cell death. The B subunit has two functions: it is responsible for toxin binding to the cell surface, and it facilitates the translocation of the A chain across the membrane and into the cytosol, where the A chain acts to kill cells.

Previously, two general types of immunotoxins have been used. Immunotoxins made with the complete toxin molecule, both A and B chains, have the complication of non-specific killing mediated by the toxin B chain binding site. This can be avoided by eliminating the B chain and linking only the A chain to the antibody. However, A chain immunotoxins, although more specific, are much less toxic to tumor cells. The B chain, in addition to having a binding function, also has an entry function, which facilitates the translocation of the A chain across the membrane and into the cytosol. Since A-chain immunotoxins lack the entry function of the B chain, they are less toxic than their intact toxin counterparts containing the complete B chain. An ideal toxin for immunotoxin construction would contain the A chain enzymatic function and the B chain translocation function, but not the B chain binding function.

Two heretofore inseparable activities on one polypeptide chain of diphtheria toxin and ricin account for the failure to construct optimal reagents. The B-chains facilitate entry of the A-chain to the cytosol, allowing immunotoxins to kill target cells efficiently and bind to receptors present on most cells, imparting immunotoxins with a great degree of non-target-cell toxicity.

Some toxins have been modified to produce a suitable immunotoxin. The two best known are ricin and diphtheria toxin. Antibodies which bind cell surface antigens have been linked to diphtheria toxin and ricin, forming a new pharmacologic class of cell type-specific toxins. Ricin and diphtheria toxin are 60,000 to 65,000 dalton proteins with two subunits: the A-chain inhibits protein synthesis when in the cytosol, and the B-chain binds cell surface receptors and facilitates passage of the A subunit into the cytosol. Two types of antibody-toxin conjugates (immunotoxins) have been shown to kill antigen-positive cells in vitro. Immunotoxins made by binding only the toxin A subunit to an antibody have little non-target cell toxicity, but are often only minimally toxic to antigen-positive cells. Another type of immunotoxin is made by linking the whole toxin, A and B subunits, to the antibody and blocking the binding of the B subunit to prevent toxicity to non-target cells. For ricin, the non-target cell binding and killing can be blocked by adding lactose to the culture media or by steric restraint imposed by linking ricin to the antibody. Intact ricin immunotoxins may have only 30- to 100- fold selectivity between antigen-positive and negative cells, but they are highly toxic, and the best reagents can specifically kill a great many target cells.

Intact ricin and ricin A-chain immunotoxins have been found to deplete allogenic bone marrow of T cells, which can cause graft-versus-host diseases (GVHD), or to deplete autologous marrows of tumor cells.

Diphtheria toxin is composed of two disulfide-linked subunits: the 21,000 dalton A-chain inhibits protein synthesis by catalyzing the ADP-ribosylation of elongation factor 2, and the 37, 000-dalton B-chain binds cell surface receptors and facilitate transport of the A-chain to the cytosol. A single molecule of either a diphtheria toxin A-chain or a ricin A-chain in the cytosol is sufficient to kill a cell. The combination of these three activities, binding, translocation, and catalysis, produces the extreme potency of these proteins. The cell surface-binding domain and the phosphate-binding site are located within the carboxyl-terminal 8-kDa cyanogen bromide peptide of the B-chain. Close to the C-terminus region of the B-chain are several hydrophobic domains that can insert into membranes at low pH and appear to be important for diphtheria toxin entry.

Antibodies directed against cell surface antigens have been linked to intact diphtheria toxin or its A subunit to selectively kill antigen-bearing target cells. Antibody-toxin (immunotoxins) or ligand toxin conjugates containing only the diphtheria A-chain have relatively low cytotoxic activity. Intact diphtheria toxin conjugates can be very potent, but can also have greater toxicity to normal cells. Since the B-chain appears to facilitate entry of the A-chain to the cytosol, it is possible that its presence in whole toxin conjugates renders them more potent, although less specific. Efforts have been made to construct more potent and specific immunotoxins by separating the toxin B-chain domains involved in cell binding from the domains involved in A-chain entry.

Target cell toxicity of immunotoxins can be increased by including the toxin B-chain in the antibody-toxin complex or by adding it separately. To achieve maximal in vitro target-cell selectivity with immunotoxins containing intact ricin, lactose must be added to the medium to block non-target-cell binding and toxicity of the immunotoxin via the ricin B-chain. This approach is feasible in those clinical settings, such as bone marrow transplantation, where the target cell population can be incubated in vitro in the presence of lactose. Without blockage of the B-chain binding domain, however, whole toxin conjugates have a high degree of non-target-cell toxicity, thereby limiting their usefulness in vivo.

Construction of reagents that combine the potency of intact toxin conjugates with the cell-type selectivity of toxin A-chain conjugates may be possible if the binding site on the toxin B-chain could be irreversibly blocked. Covalent and noncovalent chemical modifications that block the binding activity of ricin intracellularly also block its entry function, suggesting that the binding and translocation functions may be inseparable.

Previously, domain deletion was unsuccessfully used in an attempt to separate the translocation and the binding functions of diphtheria toxin B-chain. Immunotoxins made with the A-chain, intact diphtheria toxin, and a cloned fragment of diphtheria toxin (MspSA) that lacks the C-terminal 17-kDa region of the B subunit were compared. The intact diphtheria conjugate was 100 times more toxic than the MspSA conjugate was, which, in turn, was 100-fold more toxic than was the diphtheria toxin A-chain conjugate. The C-terminal, 17-kDa region, which contains the cell surface binding site, therefore potentiates immunotoxin activity 100-fold. It has not been possible to determine whether this C-terminal translocation activity was distinct from the binding activity.

Laird and Groman, *J. Virol.* 19: 220 (1976) mutagenized Corynebacterium with nitrosoguanidine and ultraviolet radiation and isolated several classes of mutants within the diphtheria toxin structural gene. Leppla and Laird further characterized several of the mutant proteins and found that three of them, CRM 102, CRM103, and CRM 107, retained full enzymatic activity but had defective receptor binding.

Recombinant DNA technology has been used to improve immunotoxin efficacy at the gene level. Greenfield et al. (1984) in *Proc. Natl. Acad. Sci. USA* 80: 6953–6857, reported that they have cloned portions of diphtheria toxin and created a modified toxin which contains the N-terminal hydrophobic region of diphtheria toxin but lacks the C-terminal cysteine for ease of linking to antibodies. This fragment lacks the cell surface-binding sits of diphtheria toxin but includes most of the hydrophobic region thought to facilitate membrane transport.

Although cleavage of ricin or diphtheria toxin into A and B-chains had been thought to improve the specificity of the immunotoxins produced from the A-chain, cleavage of ricin or diphtheria toxins into A and B-chains removes the portion of the molecule containing residues important for transport into the cytosol of the cell. Specific cytotoxic reagents made by coupling toxin A subunits to antibodies have low systemic toxicity but also very low tumor toxicity. More potent reagents can be made by coupling intact toxins to monoclonal antibodies, as detailed in *J. Immunol.* 136: 93–98 and *Proc. Natl. Acad. Sci. USA* 77: 5483–5486. These reagents, however, have a high systemic toxicity due to the toxin binding to normal cells, although they can have applications in vitro in bone marrow transplantation (cf. *Science* 222: 512–515).

It was found by Youle et al., as reported in *Jour. Immunol.*, op. cit., that monoclonal antibody-intact diphtheria cell conjugates reacted quite differently from the intact ricin immunotoxins. Of the four reagents examined, a monoclonal antibody against type T3 antigen linked to diphtheria toxin (UCHT1-DT) had unique properties. This reagent showed greater selectivity in its toxicity to T cells as compared to stem cells than UCHTl-ricin. UCHTl-DT was found to be 10 to 100 times more selective than any previously reported immunotoxin.

Neville et al., in U.S. Pat. Nos. 4,359,457 and 4,440,747, disclose that the receptor specificity of toxins can be altered by coupling the intact toxin to monoclonal antibodies directed to the cell surface antigen Thy 1.2. However, the only toxin specifically disclosed to be treated in this manner is ricin. The same inventors in U.S. Pat. No. 4,500,637, disclose the covalent linkage of a monoclonal antibody known as TA-1 directed against human T-cells for use in treating human donor bone marrow before the marrow is fused into a human recipient. Thus, this reagent has been found to be useful in preventing graft versus host disease.

Another method of treating ricin to increase the rate of protein synthesis inhibition is by adding excess ricin B-chain to target cells independent of the amount of ricin A-chain bound to the cell surface membrane. The ricin A-chains used in this procedure are conjugated to anti-Thy 1.1 monoclonal antibodies. This process is disclosed in Neville et al., U.S. Pat. No. 4,520,011.

Yet another method of treating graft versus host disease is disclosed in Neville et al., U.S. Pat. No. 4,520,226. In this method, monoclonal antibodies specific for T-lymphocytes in human donor bone marrow are covalently linked to separate ricin toxin, combined in a mixture to form a treatment reagent, and combined with bone marrow removed from a human donor. The bone marrow-reagent mixture is then infused into an irradiated recipient, which virtually eliminates T-lymphocyte activity.

However, none of the prior art has shown effective immunotoxins prepared from diphtheria toxin which have the desired specificity and activity.

Summary of the Invention

It is an object of the present invention to overcome deficiencies in the prior art, such as noted above.

Further objects of the invention are to improve anti-cancer therapy and to reduce cachetin in cancer patients.

It is another object of the present invention to provide an immunotoxin with greater potency against cancer cells than previous immunotoxins, which at the same time is safer and less toxic to normal cells.

It is yet a further object of the present invention to provide an immunotoxin with greater selectivity between antigen positive and antigen negative cells than any previously described reagent.

It is another object of the present invention to provide a reagent which selectively kills cancer cells.

It is yet anther object of this invention to provide a reagent for treating graft-versus-host disease.

It is a still further object of the present invention to provide a reagent which is particularly efficacious against neural tumors, including medulloblastoma and glioblastomas.

It is still another object of the present invention to provide a diphtheria conjugate wherein the cell recognition moiety is anti-transferrin receptor monoclonal antibody.

It is yet another object of the present invention to provide a reagent which selectively kills glioblastoma- and medulloblastoma-derived cell lines.

It is still a further object of the present invention to provide an antibody-toxin conjugate which can be used to treat CSF-borne primary or metastatic tumors.

According to the present invention, a binding, or cell recognition, moiety, which can be a monoclonal antibody such as UCJTl, transferrin, anti-transferrin receptor monoclonal antibody or anti-epidermal growth factor or any other binding agent which binds specifically to a cell, cell type, or specific receptor, is coupled to a toxin in which the native toxin binding site has been inactivated. This provides extremely potent and specific agents against cancer cells, and is particularly effective in treatment of graft versus host disease and neural tumors, including medulloblastomas and glioblastomas.

More specifically, immunotoxin conjugates are provided consisting of a toxin such as diphtheria toxin having one or two point mutations which toxin is coupled to a binding agent such as anti-transferrin monoclonal antibodies, or to transferrin. This conjugate is particularly toxic toward human medulloblastoma or glioblastomas cells.

DETAILED DESCRIPTION OF THE DRAWINGS

Figure 1A:
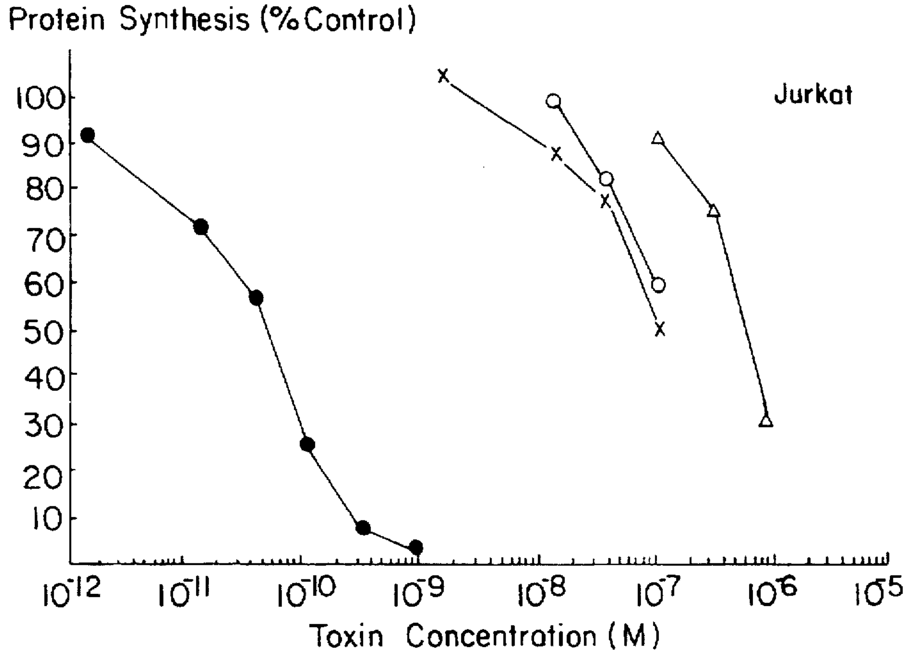
FIG. 1A shows a comparison of the toxicity of diphtheria toxin, CRM102, CRM103, and CRM107 in vitro as compared to native diphtheria toxin using a sixteen hour protein synthesis assay.
Figure 1B:
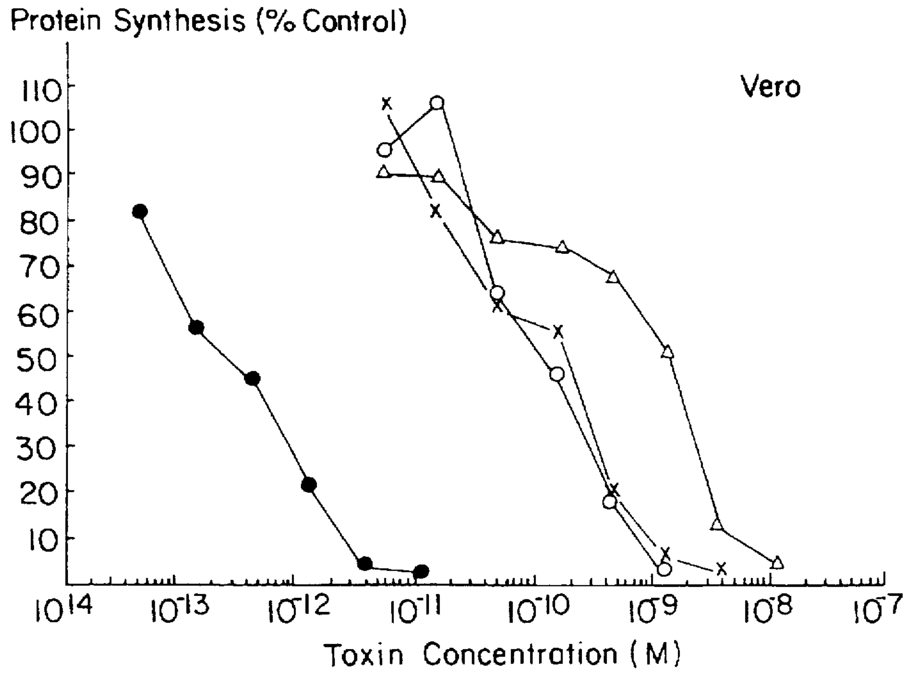
FIG. 1B shows toxicity for the diphtheria toxins as in FIG. 1A, but upon Vero cells. Panel A shows the in vitro toxicity tested on Jurkat cells, panel B shows in vitro toxicity tested on Vero cells.

In FIG. 1, protein synthesis was assayed by incubating $5\times10^4$ Jurkat cells in 100 microliters leucine-free RPMI 1640 medium containing 2% FCS in 96-well microtiter plates. DT (●), CRM102 (X), CRM103 (○), or CRM107(Δ) were added in 11 microliters buffer and incubated with cells for 16 hours at 37° C. Cells were then pulsed with 20 microliters of phosphate buffered saline containing 0.1 microCi of $^{14}$C-leucine, incubated for one hour at 37° C., harvested onto glass fiber filters by means of a PHD cell harvester, washed with water, dried, and counted. The results are expressed as a percentage of the $^{14}$C-leucine incorporation in mock-treated control cultures.

Figure 2:
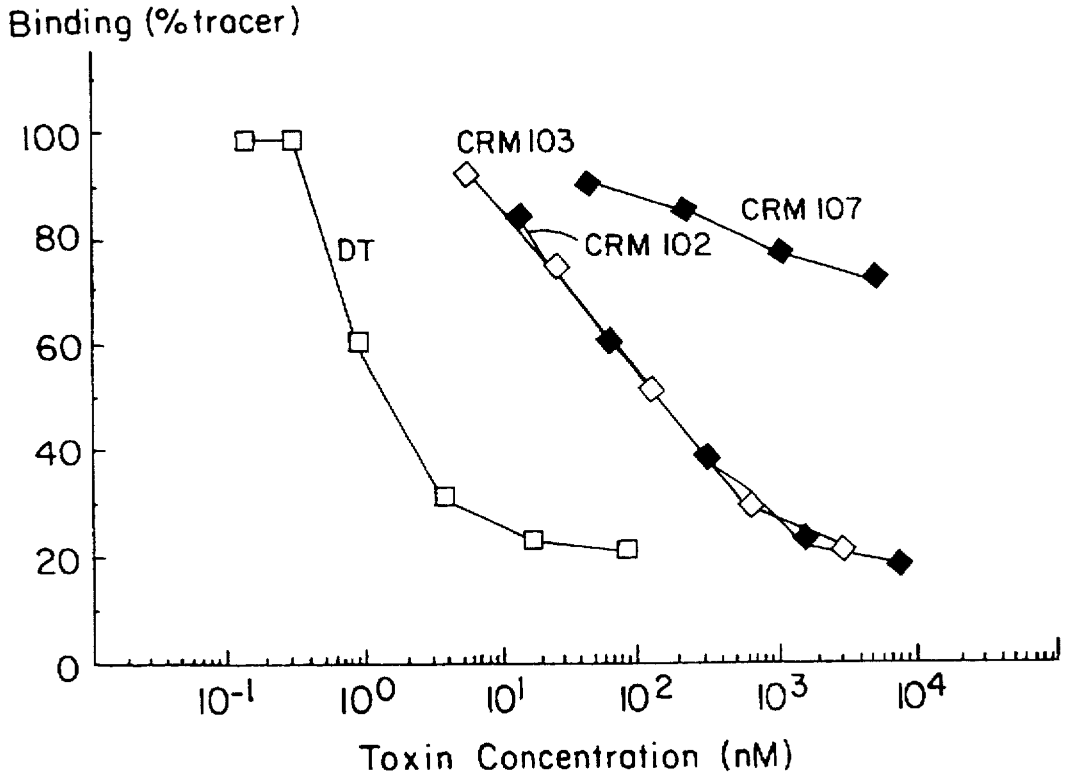
FIG. 2 shows the binding activity of native diphtheria toxin and the three CRM mutants to Vero cells.

In FIG. 2, tracer $^{125}$I-labelled DT binding was competed with cold DT (●), CRM102(X), CRM103 (○), and CRM107 (Δ). DT was labelled with Biobeads to $7\times10^6$ cpm/microgram. Vero cells, plated that previous day at $5\times10^5$ cells/ml well in Costar 24-well plates, were incubated in 150 microliters DMEM and 10% FCS and 25 mM HEPES, pH 7.0, with 8 ng/ml $^{125}$ I-labelled DT and appropriate concentrations of DT and CRMs. After incubating 6.5 hours at 4° C., the cells were washed four times in complete medium, solubilized in 0.1N NaOH, and counted. Tracer binding varied between 900 and 1500 cpm, depending upon the experiment. No nonspecific binding was subtracted.

Figure 3:
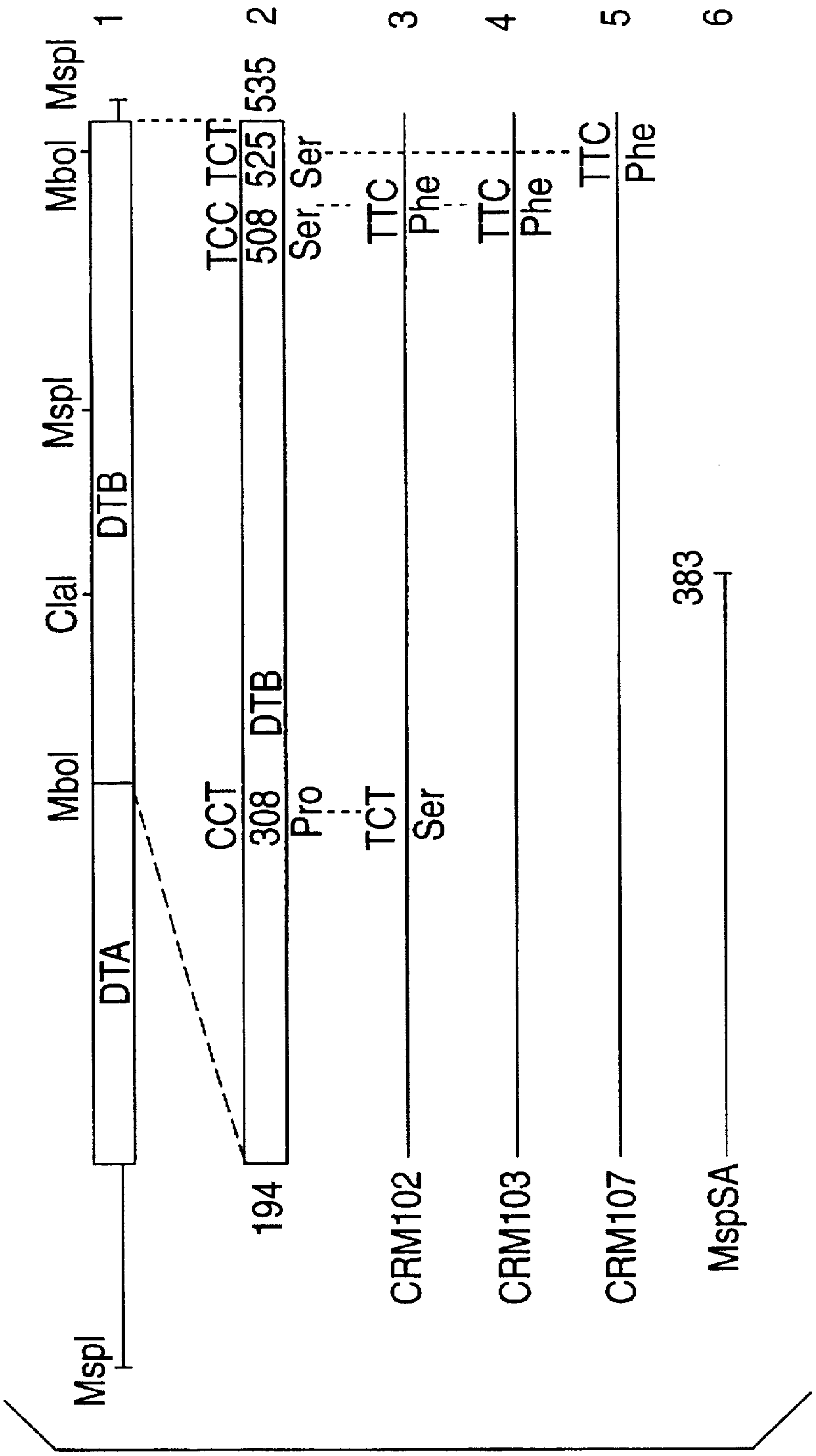
FIG. 3 shows the location of the CRM point mutations within the diphtheria toxin structural gene.

In FIG. 3, line 1 shows the restriction map of the DT structural gene, Indicating the location of the sites used for sequencing. Line 2 shows expansion of the B-chain structural region, indicating the native amino acid and DNA sequencing corresponding to the point mutations found within the CRMs. Mutations found within the B chain of CRM102, line 3, CRM103, line 4, and CRM107, line 5, are shown. Line 6 shows the end of the MspTR clone previously described. The sequences were obtained by cloning the two MboI-ClaI fragments into M13MP and M13MP19 and sequencing by the method of Sanger or by cloning the two MspI fragments into DBR322 and sequencing by the method of Gilbert and Maxam.

Figure 4:
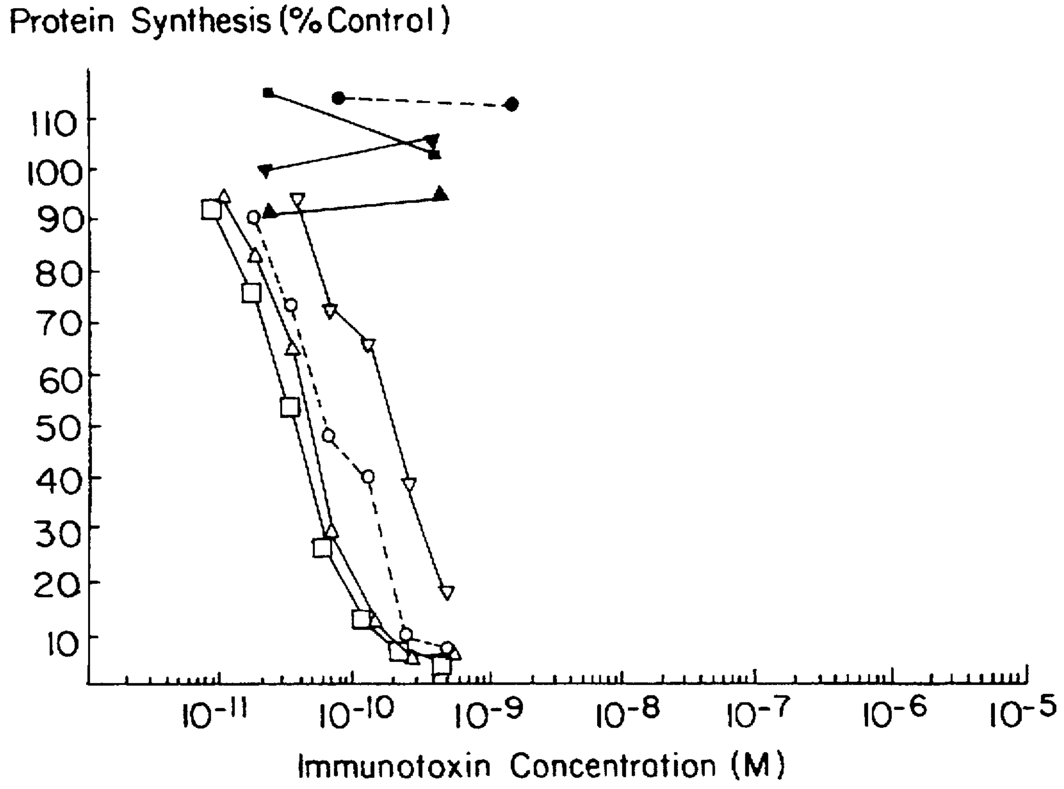
FIG. 4 shows a comparison of the toxicities of immunotoxins made by conjugating UCHT1 antibody with CRM102, CRM103, and native diphtheria toxin.

In FIG. 4, the antibody was linked to the toxins via a thioether bond as described below. Immunotoxins were separated from unconjugated Ab and toxin by gel filtration on a TSK-3000 HPLC column. The immunotoxin peak was collected, and toxicity was evaluated with the protein synthesis assay described in the legend to FIG. 1. UCHTI-DT (○), UCHTI-CRM102 (∇), UCHTI- CRM103 (Δ), and UCHTI-CRM106 (□), were incubated with $5\times10^4$ Jurkat cells for sixteen hours, followed by a one hour pulse with $^{14}$C-leucine. Incubation with excess free UCHTI (100 micrograms/ml) blocked toxicity (closed symbols).

Figure 5:
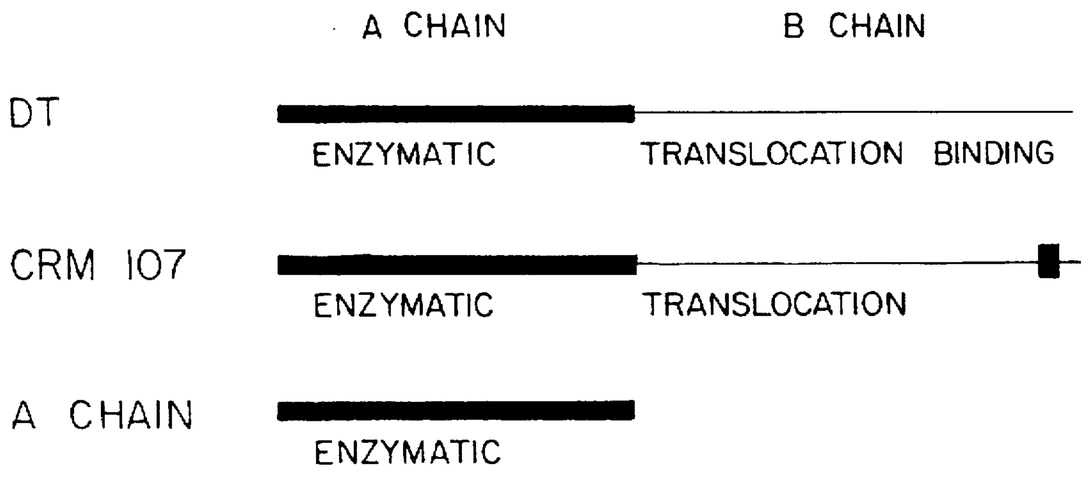
FIG. 5 is a diagrammatic representation of DT, CRM107, and DT A chain structure and function.

In the diagram shown in FIG. 5, native DT is composed of an A and B subunit with the A chain containing the enzymatic function and the B chain containing the binding and translocation function. Two point mutation in CRM107 inactivates the toxin binding function but leave the translocation and enzymatic function intact. Toxin A chain contains only the enzymatic function.

Figure 6A:
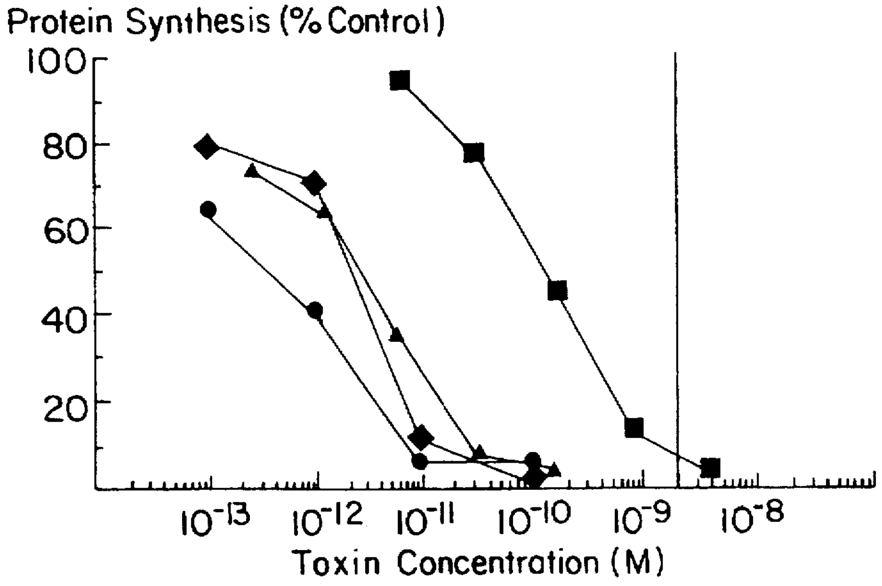
FIGS. 6A–B shows the cytotoxic effects of Tf-CRM107 on cells derived from medulloblastoma (A) and glioblastoma (B) compared to maximum tolerable levels achieved in the CSF of rhesus monkeys. Panel A shows the effect in medulloblastoma cells, panel B shows the effect in glioblastoma cells.
Figure 6B:
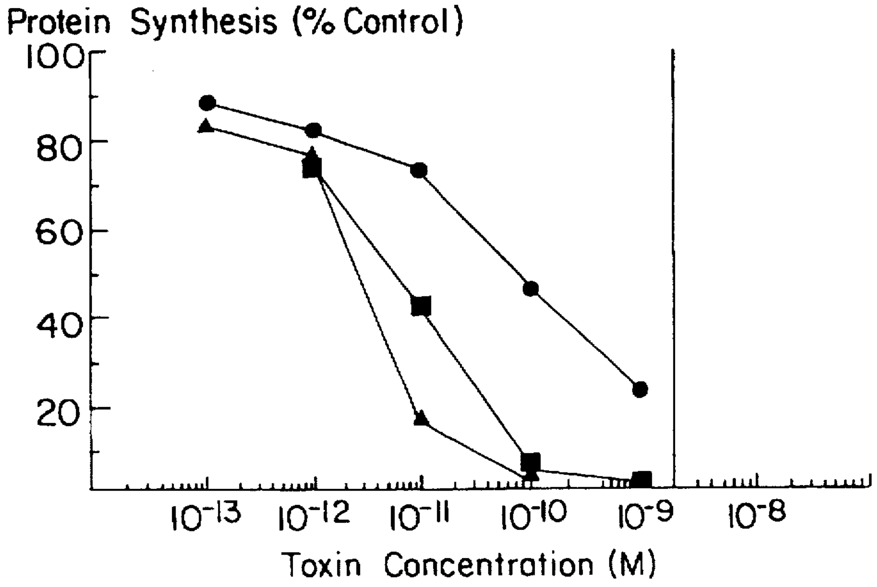

In FIG. 6, primary cultures or established cell lines were incubated for 24 hours with varying concentrations of Tf-CRM107 followed by one hour incubation with 0.1 microCi $^{14}$C-leucine. Cells from triplicate cultures were then harvested and protein synthesis in treated cells was expressed as a percentage of $^{14}$C-leucine incorporated into untreated control cells. Concentrations of $2\times10^{-9}$ of Tf-CRM107, injected intrathecally into the cisterna magna of Rhesus monkeys, could be reached safely (vertical line). FIG. 6A shows the dose response curves for medulloblastoma-derived cells, SNB105; SNB104; TE671; SNB40. FIG. 6B shows the dose response curves for glioblastoma-derived cells: SNB75; U251; SNB101.

Figure 7A:
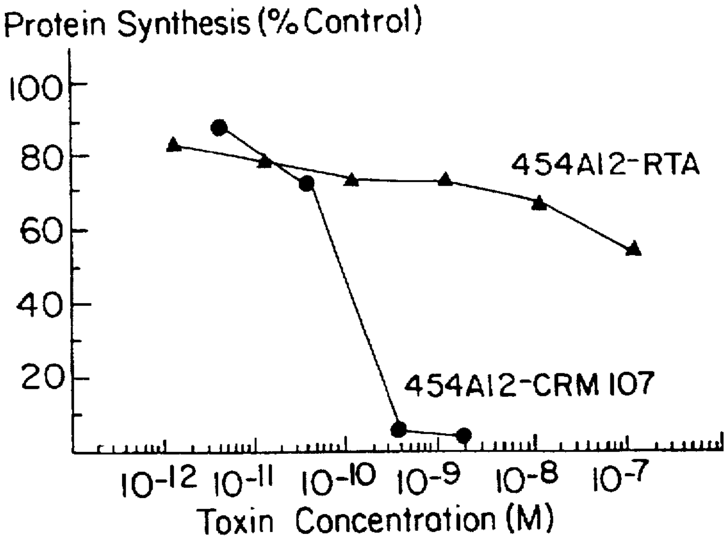
FIGS. 7A–C shows a comparison of the toxicity of 454A12 linked to CRM107 or to ricin A chain in various cell lines. Panel A shows the effect in medulloblastoma cells, panel B shows the effect in glioblastoma cells and panel C shows the effect in breast carcinoma cells.
Figure 7B:
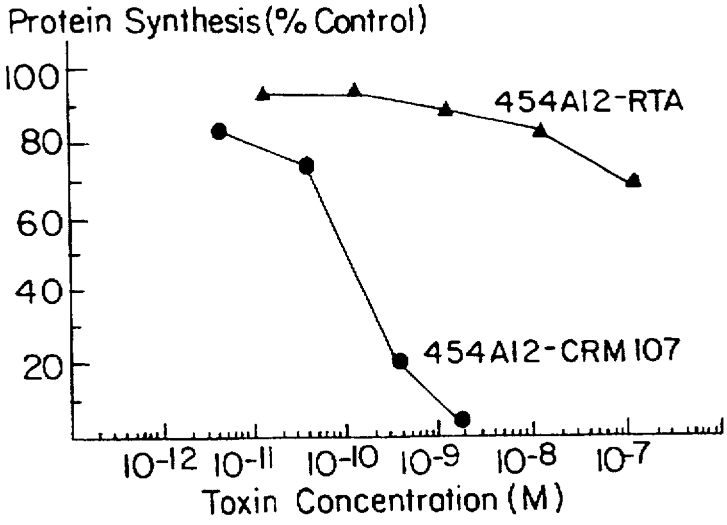
Figure 7C:
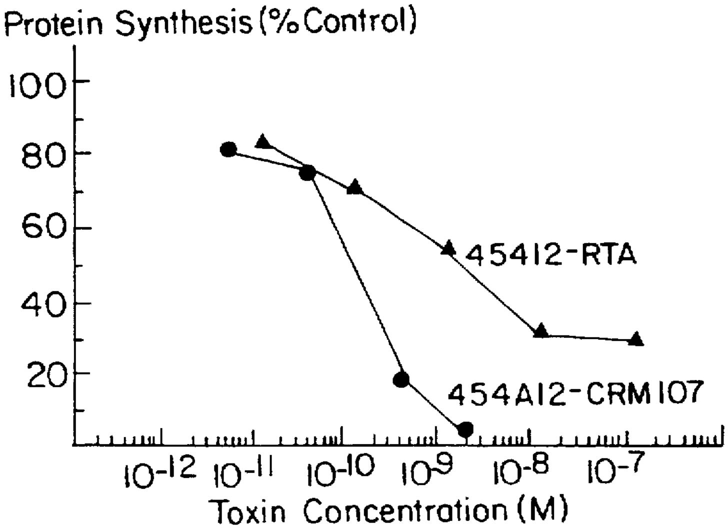

FIG. 7 shows cell lines derived from medulloblastoma (TE671; FIG. 7A), glioblastoma (U251, FIG. 7B, or breast carcinoma (T47D, FIG. 7C) were incubated with 454A12 immunotoxins for four hours followed by one hour pulse with $^{14}$C-leucine. The cells were harvested and protein synthesis in treated cells was expressed as a percentage of $^{14}$C-leucine incorporated into untreated control cells.

Figure 8A:
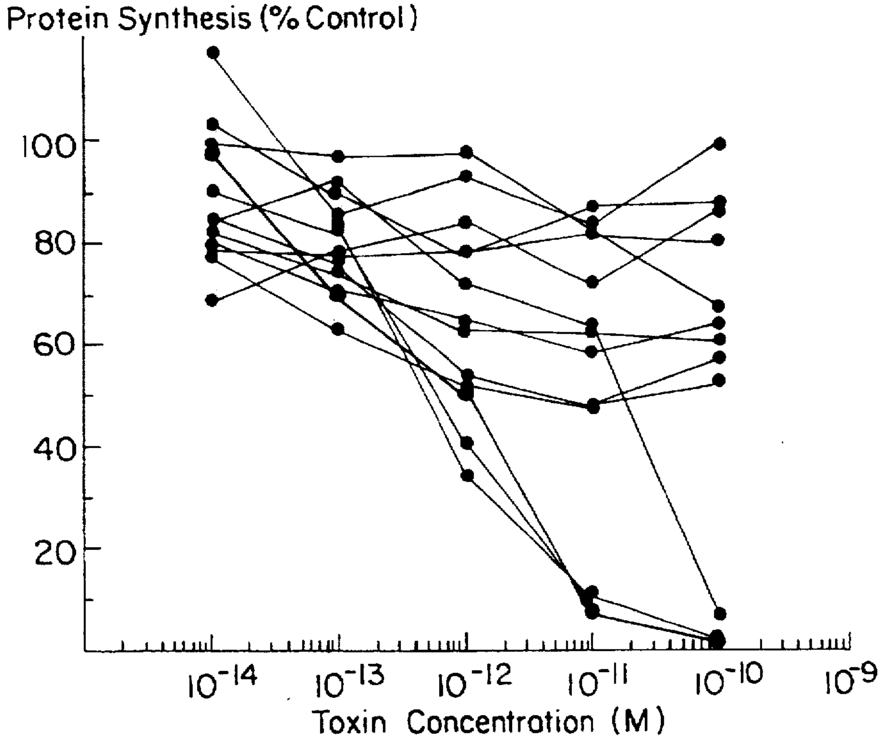
FIGS. 8A–B shows the inhibition of DT cytotoxicity by human serum or CSF. Effects of pre-incubation of the DT with serum are shown in panel A. Effects of pre-incubation of DT with CSF are shown in panel B.
Figure 8B:
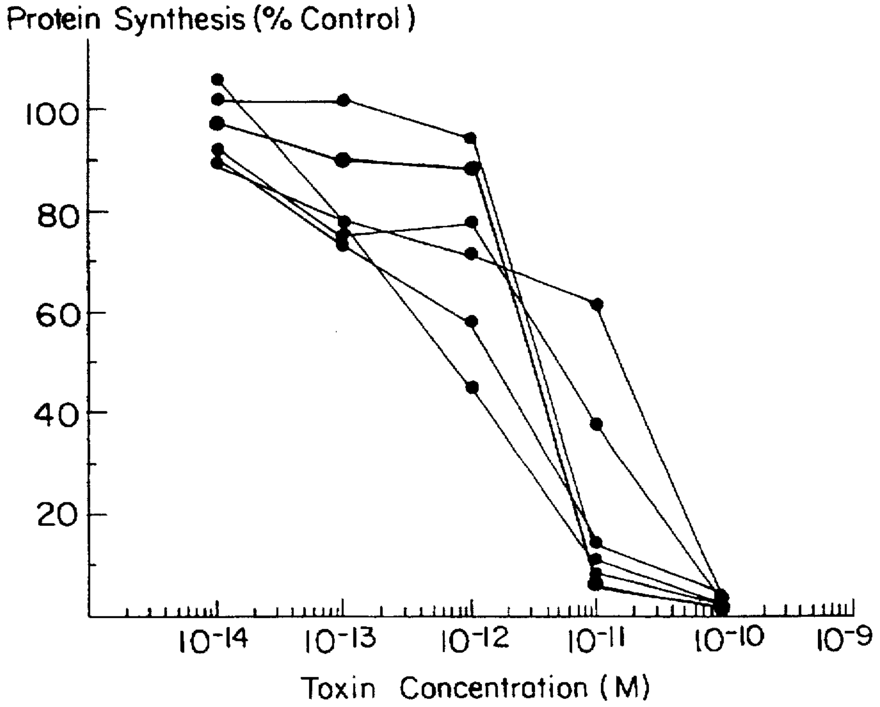

In FIG. 8, Vero cells, derived from green monkey kidney, have high levels of DT receptors ($1.6\times10^5$ sites per cell) and as a result are extremely sensitive to DT toxicity. Vero cells were therefore used to determine the presence of anti-DT antibodies in the serum and CSF of normal volunteers. Dilutions of DT were preincubated with an equal volume of undiluted serum or CSF for thirty minutes at room temperature. Twenty-two microliters of the preincubated DT mixtures were added to the Vero cells and incubated for fourteen hours. Cytotoxicity assays were performed and the results were expressed as described in the Detailed Description of the Invention. DT control, preincubated with PBS rather than serum or CSF, is plotted as a bold line. The effect of preincubation of DT with serum, FIG. 8A, or CSF, FIG. 8B, from normal volunteers is shown by thin lines.

Figure 9:
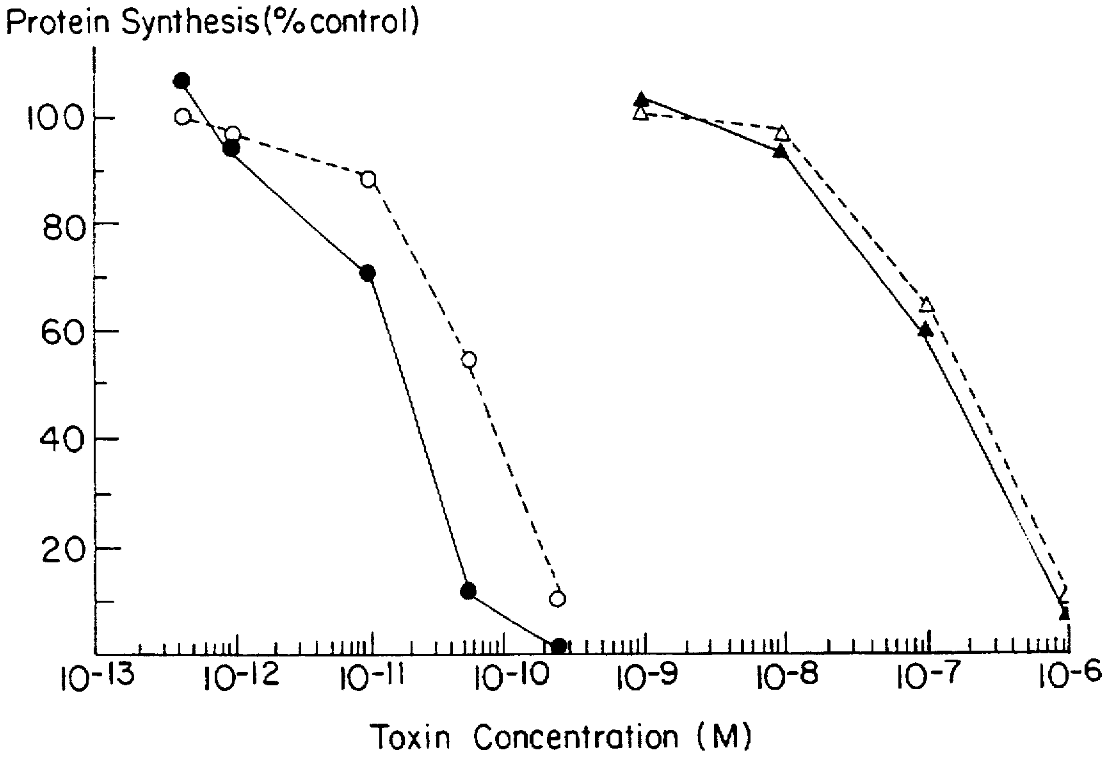
FIG. 9 shows inhibition of toxicity by free Tf.

FIG. 9 shows the inhibition of cytotoxicity by free Tf. The human erythroblastoma-derived cell line, K562, has been shown to express high levels of TfR ($1.5\times10^5$ sites per cell), and as a result is extremely sensitive to the Tf-CRM conjugate. The effect of 15 micrograms/ml Tf, reported to be the level found in human CSF on the cytotoxicity of DT and Tfn-CRM 107 was therefore evaluated using K562 cells. Cells in leucine-free media without fetal calf serum were incubated with diferric Tf, producing a final concentration of 15 micrograms/ml. PBS was added to control wells. Dilutions of Tfn-CRM107 to native DT were added and the cells were incubated for five hours at 37° C. Cytotoxicity assays were performed and the results were expressed as described infra. Tf-CRM107; Tfn-CRM107+14 microg/ml Tf; DT; DT+14 microg/ml Tf.

DETAILED DESCRIPTION OF THE INVENTION

The present invention provides mutants of diphtheria toxin which are conjugated to a binding moiety which is a binding agent which binds specifically to a cell, cell type, or specific receptor. The binding agent may be a monoclonal antibody, transferrin, or epidermal growth factor, for which receptors are found in a great variety of human tumor cells. The conjugates of the present invention can be used to prepare formulations for treating a great variety of tumors without the undesirable effects of native diphtheria toxins on the patients.

More specifically, immunotoxin conjugates are provided consisting of diphtheria toxin or a like toxin having one or two point mutations, coupled to either anti-transferrin receptor monoclonal antibodies, or transferrin. This conjugate is particularly toxic towards human medulloblastoma or glioblastoma cells, and thus is particularly useful in treating neurological tumors.

Immunotoxins were made by conjugating three forms of diphtheria toxin, CRM102, CRM103, and CRM107 (cf. *J. of Virology* 19: 220–227, 1976) that differ in only one or two amino acids from native diphtheria toxin in the C region, with UCHTI, a monoclonal antibody to the T3 antigen receptor found on human T-cells, or to transferring or to any one of a number of known binding agents such as epidermal growth factor and polyclonal sera of certain types. The conjugation used a slight modification of previously published procedures, PNAS, 77: 5483–5486, (1980).

The phenotypic designation CRM is used to designate the protein product of a tox gene that is serologically identical with diphtheria toxin.

The nontoxinogenic mutants of corynebacteriophage beta have been classified into four major classes. Class I consists of ten mutants, each of which produces a protein that forms a line of identity with diphtheria toxin when tested by immunodiffusion against diphtheria antitoxin. These mutants probably represent nonsense mutations in the structural gene for toxin. The mutants in subclass 1A give a positive skin test but a negative tissue culture test. Two possible explanations are that the mutant protein has a low level of activity or is produced in smaller amounts.

Class II mutants produce proteins that form lines of partial identity with toxin when tested against antitoxin by immunodiffusion. On slab gel electrophoresis, only one of these proteins was detected, but, based on immunodiffusion tests, all appear to be smaller than purified toxin. Either a deletion, a nonsense mutation in the structural gene for toxin, or preferential proteolysis could account for the shortened polypeptide.

Class III mutants produce two proteins serologically related to toxin, two lines being detected in the immunodiffusion test. One line shows full identity with purified toxin, and the other shows only partial identity.

Class IV mutants do not produce a protein serologically related to toxin, nor are they capable of eliciting a positive guinea pig skin test. The phenotype of these mutants has been designated CRM-. This would indicate that the intact toxin molecule is either not produced or is produced or excreted in very small amounts. This CRM-phenotype couple results from such mutational events as a deletion, a very early nonsense mutation in the toxin structural gene leading to the production of small fragments of toxin, or a mutation in a regulatory site or gene.

The CRM102, CRM103, AND CRM 107 have not been classified in one of the four major classes of mutants of diphtheria toxin, although immunodiffusion shows complete antigenic homology with diphtheria toxin. The molecular weight of these three CRM's was determined by electrophesis to be in the range of about 62,000.

Diphtheria toxin and CRM102, CRM103, and CRM107 were conjugated to m-maleimidobenzoyl N-hydroxysuccinimide ester (MBS) by incubating the toxins with a 10-fold excess of MBS for thirty minutes at room temperature. The mixture was then applied to a G-25 column to remove free MBS from the toxin. UCHTl was reduced with 10 mM dithiothreitol for 30 minutes at room temperature, and free DTT was separated from the antibody on a G-25 column. MBS-conjugated toxin was mixed with reduced antibody and incubated at room temperature for three hours. Immunotoxins were separated from unconjugated antibody and toxin by gel filtration on a TSK-3000 HPLC column.

Peak fractions containing the immunotoxins were collected and tested for toxicity to an antigen positive human leukemic T-cell line. Protein synthesis was assayed by incubating $10^5$ cells in 100 microliters of leucine-free RPMI 1640 containing 2% fetal calf serum in 96 well microtiter dishes. Toxins, immunotoxins, and control buffers (11 microliters) were incubated with the cells for sixteen hours at 37° C. Twenty microliters of phosphate buffered saline containing 0.1 microCurie of $^{14}$C-leucine was then added for 60 minutes. Cells were harvested onto glass fiber filters using a PHD cell harvester, washed with water, dried, and counted. The results are expressed as percentage of $^{14}$C incorporation in mock-treated control cultures.

FIG. 1 shows the toxicity of CRM102, CRM103, CRM104, and native diphtheria toxin to Jurkat cells (A) and Vero cells (B). Protein synthesis was assayed by incubating $5\times10^4$ Jurkat cells in 100 microliters leucine-free RPMI 1640 medium containing 2% FCS in 96-well microtiter plates.

DT (●), CRM102 (X), CRM103 (○), or CRM107 (Δ) were added in 11 microliters buffer and incubated with cells for 16 hours at 37° C. The cells were then pulsed with 20 microliters of PBS containing 0.1 microCurie of $^{14}$C-leucine, incubated for one hour at 37° C., harvested onto glass fiber filters by means of a PHD cell harvester, washed with water, dried, and counted. The results are expressed as a percentage of the $^{14}$C-leucine incorporation in mock-treated control cultures.

Vero cells have a higher Lumber of diphtheria toxin receptors than do Jurkat cells, and are thus more sensitive to diphtheria toxin inhibition of protein synthesis than are Jurkat cells. CRM102 and CRM103 are 1000-fold less toxic than native diphtheria toxin is, and CRM107 is 10,000-fold less toxic than native diphtheria toxin is to both Vero cells and Jurkat cells.

FIG. 2 shows the binding activity of native diphtheria toxin and the three CRM mutants to Vero cells. While most cell types, including lymphoid cells such as Jurkat, have undetectable levels of diphtheria toxin receptors, Vero cells contain $10^5$ diphtheria toxin receptors per cell and have been used extensively to study diphtheria toxin binding. At 4° C. the affinity of both CRM102 and CRM103 is 100-fold less than that of native diphtheria toxin, and the affinity of CRM107 is 8000-fold less than that of native diphtheria toxin.

The reduced affinity correlates with the reduced toxicity for CRM107 but differs by 10-fold for CRM102 and CRM103. Binding was determined after six hours at 4° C., while toxicity was determined after 24 hours at 37° C. The discrepancy between binding and toxicity for CRM102 and CRM103 may reflect differences in temperature and time in the two assays. Binding cannot be determined at 37° C. since energy inhibitors commonly used to block internalization decrease the number of surface diphtheria toxin receptors. Alternatively, the mutations within CRM102 and CRM103 may inhibit toxin activities other than binding that may account for the 10-fold difference between toxicity and binding.

FIG. 3 shows the location of the amino acid changes within the B-chain for each of the three mutations. CRM103 contains a single mutation at position 508 (Ser-PHE). CRM102 contains a similar mutation at position 508, but has an additional mutation at position 308 (Pro-Ser). CRM107 contains a mutation at position 525 (Ser-Phe). That CRM102 has two mutations while CRM103 contains only one indicates that the two mutants are independent isolates. The presence of multiple GC-AT transitions is consistent with nitrosoguanidine-induced mutagenesis.

Line 1 is the restriction map of the diphtheria toxin structural gene, indicating the location of the sites used for sequencing. Line 2 is the expansion of the B-chain structural region, indicating the native amino acid and DNA sequence corresponding to the point mutations found within the CRM's. Mutations found within the B-chain of CRM102 (line 3), CRM103 (Line 4), and CRM107 (line 5) are shown. Line 6 shows the end of the MspRT clone previously described. The sequences were obtained by cloning the two MboI-ClaI fragments into M13MP and M13MP19 and sequencing by the method of Sanger et al., J. Mol. Biol. 162, 729 (1982), or by cloning the two MspI fragments into pBR322 and sequencing by the method of Gilbert and Maxam, Methods Enzymol. 65, 499 (1980).

The 100-fold decreased binding affinity of CRM103 and CRM102 demonstrates that the serine at position 508 is important for toxin binding. The data suggest that the alteration at position 525 causes the 8000-fold decrease in binding activity. The mutations at positions 508 and 525 are consistent with data which suggest that the diphtheria toxin binding domain lies within the carboxyl 17-kDa portion of the molecule. Both mutations exchange a phenylalanine for a serine.

The relationship of binding to translocation in diphtheria toxin was examined by linking each of the CRM's and native diphtheria toxin to a new binding domain, the monoclonal antibody UCHT1, which is specific for the T3 antigen on human T-cells.

FIG. 4 shows that, unlike the unconjugated CRM's, all three CRM immunotoxins are highly toxic. Excess antibody blocks toxicity, demonstrating that the toxicity is antibody-mediated. The immunotoxins prepared with CRM103 and CRM107 are equally toxic as the immunotoxin prepared with native diphtheria toxin, whereas the immunotoxin prepared from CRM102 is approximately 10-fold less toxic. The 10-fold decrease in UCHT1-CRM102 toxicity relative to UCHT1-CRM103, despite identical binding activity of CRM102 and CRM103, suggests that the amino acid at position 308 contributes to the translocation activity of diphtheria toxin. That the conjugates prepared with CRM103 and CRM107 are as toxic as are conjugates prepared with native diphtheria toxin indicates that binding of the toxin to its receptor is not necessary for efficient translocation of the toxin-A fragment to the cytosol. Therefore, the diphtheria toxin binding and translocation functions can be separated.

FIG. 4 shows the comparison of the toxicities of immunotoxins made by conjugating UCHT1 with CRM102, CRM103, CRM107, and native diphtheria toxin. The antibody was linked to the toxins via a thioether bond as described previously. Immunotoxins were separated from unconjugated antibody and toxin by gel filtration on a TSK-3000 HPLC column. The immunotoxin peak was collected, and toxicity was evaluated with the protein synthesis assay as described in FIG. 1. UCHT1-DT (○), UCHT1-CRM102 (∇), UCHT1-CRM103 (Δ), and UCHT1-CRM107 (□) were incubated with $5\times10^4$ Jurkat cells for sixteen hours, followed by a one hour pulse with $^{14}$C-leucine. Incubation with excess free UCHT1 (100 micrograms/ml) blocked toxicity.

As shown in both FIGS. 1 and 4, native diphtheria toxin and UCHT1-diphtheria toxin inhibit Jurkat cell protein synthesis 50% at $3\times10^{-11}$M. The selective toxicity of UCHTl-DT to T3 bearing cells is 100-fold, and exists solely because crosslinking diphtheria toxin to antibody inhibits diphtheria toxicity 100-fold. The mutant toxins, CRM102, CRM103, and CRM107, inhibit Jurkat cell protein synthesis 50% at $1\times10^{-7}$M to $4\times10^{-6}$M (FIG. 1), whereas the UCHTl-CRM immunotoxins act at $3\times10^{-11}$M to $3\times10^{-10}$M (FIG. 4). This 1000–10,000-fold difference in concentration between the CRM's and the UCHTl-CRM's required to inhibit protein synthesis represents a three to four order of magnitude increase in CRM immunotoxin selectivity over the native diphtheria immunotoxin.

The toxicities of the different immunotoxins were compared on non-target Vero cells, which lack antibody-binding sites but express a high number of diphtheria toxin cell-surface binding sites. UCHTl-DT inhibits Vero protein synthesis 90% at $6\times10^{-10}$M, because of toxicity via the diphtheria toxin binding site. In contrast, all three CRM immunotoxins had no effect on protein synthesis at this concentration. Thus, the loss of toxicity of the CRM's, as shown in FIG. 1, is exhibited also by the CRM immunotoxins on non-target cells.

The immunotoxins as described herein can also be conjugated with human transferrin (Tfn). Transferrin is highly conserved across species, and, as a result, human transferrin exhibits species cross-reactivity that enables the comparison of the toxicity of transferrin-toxin conjugates on cells derived from human (Jurkat, K562), monkey (Vero), and mouse (Wehi, EL-4), as shown in Table 1.

in 1:1.3 molar ratio and incubated for three hours at room temperature. Immunotoxins were purified by gel filtration on a TSK-3000 HPLC column.

Species cross-reactivity enables one to evaluate the toxicity and the effectiveness of the toxin conjugate in animal models as well as to examine the effectiveness of the Tfn-toxin conjugate in a wide variety of human tumors. Tfn-CRM107, when assayed on Jurkat cells, exhibited a 400,000-fold differential in toxicity over CRM107 alone. This represents a considerable improvement in the 10,000-fold selectivity previously observed between UCHTl-CRM107 and CRM107 on Jurkat cells.

It has also been found that K562, a human erythroleukemia cell line characterized by high levels of transferrin receptors, is also sensitive to Tfn-CRM107. Assuming that the binding and toxicity of CRM107 is reduced by 10,000-fold relative to diphtheria toxin on K562 cells, as it is on Vero and Jurkat cells, then the differential in toxicity between CRM103 and Tfn-CRM107 for K562 cells is greater than one million. Binding of the toxin conjugates was Tfn-mediated as shown by the fact that free Tfn completely inhibits toxicity, as shown in Table 2.

TABLE I $IC_{50}$ of DT and Tfn-Toxin Conjugates on Various Cell Lines

| Cell Line | Source | DT | Tfn-DT | Tfn-CRM107 | CRM107 |
|---|---|---|---|---|---|
| Vero | Monkey kidney | $8 \times 10^{-13}$ M[(a)] | $1.9 \times 10^{-11}$ M | $1.4 \times 10^{-10}$ M | $8 \times 10^{-9}$ M |
| K562 | Human Erythroleukemia | $3.4 \times 10^{-10}$ M | $9 \times 10^{-13}$ M | $1.6 \times 10^{-12}$ M | $3.4 \times 10^{-6}$ M[(c)] |
| Jurkat[(b)] | Human T-cell leukemia | $6.1 \times 10^{-11}$ M | $4 \times 10^{-12}$ M | $2 \times 10^{-12}$ M | $5.4 \times 10^{-7}$ M |
| EL-4 | Mouse T-cell lymphoma | $2.8 \times 10^{-7}$ M | $1.6 \times 10^{-11}$ M | $8 \times 10^{-12}$ M | $2.8 \times 10^{-3}$ M[(c)] |
| Wehl | Mouse T-cell lymphoma | $2.4 \times 10^{-7}$ M | $4.8 \times 10^{-12}$ M | $8.5 \times 10^{-12}$ M | $2.4 \times 10^{-3}$ M[(c)] |
| MCF7 | Human breast adenocarcinoma | $1.1 \times 10^{-11}$ M | $2.8 \times 10^{-11}$ M | $1 \times 10^{-10}$ M | |
| TE61 | Human medulloblastoma | $3.7 \times 10^{-11}$ M | | $3.5 \times 10^{-12}$ M | |
| SNB 40 | Human medulloblastoma | $1.7 \times 10^{-11}$ M | | $1.4 \times 10^{-11}$ M | |
| SNB 75 | Human glioblastoma | $4.6 \times 10^{-13}$ M | | $5.0 \times 10^{-12}$ M | |

[(a)]Concentrations shown are the concentrations that inhibit protein synthesis by 50% of control values.
[(b)]Jurkat cells were incubated with toxins for 16 hrs, followed by a 1 hr pulse with $^{14}$C—Leu. All other cell lines were incubated for 24 hrs followed by a 1 hr pulse.
[(c)]These concentrations are assumed, based on the 10,000-fold reduction in CRM107 toxicity observed in both Vero and Jurkat cells. Limtations imposed by the concentration of CRM107 did not permit direct measurement.

Before conjugating the toxin with transferrin, human transferrin (Tfn) was loaded with iron according to the method of Shindelman et al., (1981), *Int. J. Cancer* 27: 329. The conjugation of Tfn was accomplished by first generating free sulfhydryl groups on Tfn with 2-iminothiolane. The 2-iminothiolane was dissolved in 0.8M boric acid, pH 8.5, and incubated with Tfn in an 8:1 molar ratio. After a one hour incubation at room temperature, the modified Tfn was separated from the 2-iminothiolane by gel filtration on a G-25 column. M-maleimidobenzoyl N-hydroxysuccinimide (MBS) was dissolved in dimethylformamide and added in five-fold molar excess to the toxin, which was either native diphtheria toxin, CRM102, CRM103, or CRM107. This mixture was incubated for thirty minutes at room temperature, and free MBS was removed from the toxin by chromatographic separation using a G-25 column. The MBS-conjugated toxin was mixed with thiolated transferrin

TABLE 2

INHIBITION OF TOXICITY BY FREE UCHT1 OR TFN

| Toxin | Cell Line | Protein Synthesis % Control |
|---|---|---|
| UCHT1 - CRM107 ($4 \times 10^{-10}$ M) | Jurkat | 3.9 |
| UCHT1 - CRM107 ($4 \times 10^{-10}$ M) + free UCHT1 (100 ug/ml) | Jurkat | 94.5 |
| Tfn - CRM107 ($3.6 \times 10^{-10}$ M) | K562 | 0.7 |
| Tfn - CRM107 ($3.6 \times 10^{-10}$ M) + free Tfn (300 ug/ml) | K562 | 100.3 |
| Tfn - DT ($2.3 \times 10^{-10}$ M) | K562 | 2.4 |
| Tfn - DT ($2.3 \times 10^{-10}$ M) + free Tfn (300 ug/ml) | K562 | 110.3 |

Established Cell Lines

The SNB 75 cell line was established by primary explants from a tumor removed from a 72 year old woman with a bifrontal glioblastoma multiforme. SNB 101 was also established by primary explants from a glioblastoma multiforme removed from right parietal lobe of a 49-year-old man. SNB 40 was derived from primary explants of a medulloblastoma surgically removed from the posterior fossa of an eight-year-old boy. At the time the study described herein was conducted, SNB 75 was in it 48th passage, SNB 101 was in its 14th passage, and SNB 40 in its 20th passage.

U251 is a cell line of human glioma origin adapted to culture by J. Ponten and B. Westermark at the University of Uppsala, Uppsala, Sweden.

TE 671, derived from a human medulloblastoma, was obtained from American Type Culture Collection, Rockville Md. All of these cell lines were maintained in DMEM containing 105 fetal calf serum, 2 mM glutamine, 1 mM sodium pyruvate, 0.1 mM non-essential amino acids, and 10 microg/ml gentamycin.

Three cell lines from human breast cancers were examined. MCF-7, a breast adenocarcinoma-derived cell line, was maintained in DMEM containing the supplements described above plus 10 microg/ml insulin.

ZR-75-1, a cell line derived from a malignant ascitic effusion of a patient with infiltration ductal carcinoma, was maintained in RPMI 1640 containing 10% fetal calf serum, 10 mM HEPES, 20 microg/ml gentamycin, and 2 mM glutamine.

T47D, a cell line derived from an infiltrating ductal carcinoma, was grown in RPMI 1640 as described above with the addition of 10 microg/ml insulin.

Primary Medulloblastoma Cultures

Since established cell lines long adapted to culture conditions could conceivably possess transferrin requirements and receptor levels different from those of the original cells, two primary medulloblastoma cultures were established with determined sensitivity to Tf-CRM107. SNB 104 was established from a biopsy of a midline cerebellar vermian mass in an 18-year-old male. SNB 105 was derived from a midline posterior fossa tumor in a 5-year-old girl. In both cases, fresh tumor was transported to the laboratory in Eagle's Minimal Essential Medium (MEM) with 10% fetal calf serum. The tumors were mechanically and then enzymatically dissociated and were cultured at a density of 1–5×105 cells.ml in 75 cm2 tissue culture flasks. The culture medium consisted of Eagle's MEM with Earle's salts supplemented with 10% fetal calf serum, 1% non-essential amino acids, 1 mM sodium pyruvate, 2 mM L-glutamine, Penicillin (100,000 u/l), streptomycin (100 mg/l) and Fungizone (0.25 mg/l). The cultures attained 50% confluence within ten to fourteen days, at which time trypsinization, transfer to 96 well plates, an cytotoxicity testing were performed as described below.

Synthesis and Purification of CRM107 Immunotoxins

CRM107, isolated by Laird and Groman *J Virology* 19: 220–227, 1976, was purified. Human transferrin (Sigma, St. Louis, Mo.) was loaded with iron according to the method of Shindelman et al., *Int J Cancer* 27: 329–334, 1981. Conjugation of transferrin with CRM107 was accomplished by first generating free sulfydryl groups on transferrin with 2-iminothiolane. The 2-iminothiolane was dissolved in 0.8M boric acid, PH8.5 and incubated with transferrin in an 8:1 molar ratio. After one hour at room temperature, the modified transferrin was separated from free 2-iminothiolane by gel filtration on a Sephadex G-25 gel filtration column, equilibrated with PBS. The bifunctional cross-linking agent, m-maleimido-benzoyl-N-hydroxysuccininide ester (MBS) was used to link transferrin to CRM107. MBS, dissolved in dimethylformamide, was added in 5-fold molar excess to the toxin. The mixture was incubated for 30 minutes at room temperature followed by chromatographic separation on G-25. The MBS-conjugated toxin was mixed with thiolated transferrin in 1:1.3 molar ratio, incubated for three hours at room temperature, and the toxin-conjugate was purified by gel filtration on a TSK-3000 HPLC column. One minute fractions were collected and individual fractions were tested for toxicity using protein synthesis inhibition. Peak fractions of the toxin conjugate were pooled, and the A-chain in this pooled peak was quantified using the EF-2- ADP-ribosylation assay. This pooled peak was used for all further experiments.

The anti-Tfr monoclonal antibody, 454A12, was prepared as described in Frankel et al., *J Biol Response Modifiers* 4: 273–286, 1985. This monoclonal antibody was linked to CRM107 as described above. This antibody was also conjugated with recombinant ricin A chain (RTA) as described by Bjorn et al. in *Cancer Res* 45: 1214–1221, 1985.

ADP-Ribosylation Assay

The concentration of the CRM107 immunotoxins was determined using an ADP-ribosylation assay. This assay measures the ability of the CRM107 immunotoxins to catalyze the transfer of ADP-ribose from nicotinamide adenine dinucleotide to elongation factor 2 (EF-2).

The EF-2 was purified from rat liver cells following the procedure described by Youle et al. in *J Biol Chem* 254: 11089–11096, 1979. ADP-ribosylation was carried out in 80 microliter reaction mixtures containing 40 microliters 0.01M Tris-HCl buffer, with 1.0M DTT, pH 8.0 p, 20 microliters EF-2, and 10 microliters toxin sample. The reaction was initiated by addition of 10 microliters of 32P-nicotinamide adenine dinucleotide (1.2 microCI, specific activity 277 Ci/mmol, adjusted to 180 microM with cold nicotinamide adenine dinucleotide). The reactions mixtures were incubated at room temperature for 20 minutes, and the reaction was stopped by the addition of 1 ml 10% TCA. The precipitate was washed once with 10% TCA, solubilized in 0.1M NaOH, and counted.

ADP-ribosylation activities of unknown samples were compared to values obtained from DT standards consisting of known concentrations of DT (Values based on Lowry protein determination using bovine serum albumin as a standard). Tie background of the assay was determined by replacement of the toxin with Tris-HCl buffer.

Protein Synthesis Assay

Inhibition of protein synthesis was used to assay the cytotoxic effects of the toxin-conjugate. Cells were trypsinized, washed in their regular growth media, and dispersed in this media into 96-well microtiter plates at a density of 5×104 cells per well. The cells were allowed to reattach and grow in the 96-well plate for 24 hours before the assay. The cells were then washed twice with leucine-free RPMI media containing 10 mM HEPES, and 10 microg/ml gentamycin but without fetal calf serum, and the wells were refilled to a final volume of 100 microliters. Toxin conjugates, toxins alone, or control solutions were added in 11 microliter aliquots, and the cells were incubated at 17° C. for 24 hours. At the end of this incubation, 20 microliters of phosphate buffered saline containing 0.1 microCi of 14C-leucine was added, incubation continued for one hour, and the cells were harvested onto glass fiber filters using a PHD cell harvester (Cambridge Technology, Inc., Cambridge, Mass.) The filters were washed with water, dried, and counted. All cytotoxicity assays were performed 2–5 times in triplicate. The results were expressed as a percentage of $^{14}$C-leucine incorporation in the mock-treated control cultures.

In Vivo Toxicity

Guinea Pig

To investigate the efficacy of intrathecal immunotoxin therapy for tumors of the CSF compartment, the toxicity of DT or CRM107 alone, or Tf-CRM107 conjugate was determined by injecting the toxin or toxin-conjugate directly into the cisterna magna of strain 2 guinea pigs. The animals were anesthetized with intraperitoneal ketamine, 30–50 mg/kg. Toxin or conjugate, suspended in 100 microliters PBS/0.2% BSA was slowly injected percutaneously via a #25 gauge needle into the cisterna magna. The injections were performed only after CSF was clearly visualized in the hub of the needle. Final concentrations achieved in the CSF were calculated based on a total guinea pig CSF volume of 500 micoliters. The length of survival was recorded as the number of days following injection until death. Body weight was also measured at designated intervals and compared to control animals injected with PBS alone.

Rhesus Monkey

A single dose of Tf-CRM107 in 0.5 cc normal saline containing 0.2% human serum albumin was administered to anesthetized adult Rhesus monkeys by occiputal puncture and gentle babbotage. This technique is known to effect rapid mixing of injectant with cisternal and ventricular cerebrispinal fluid. Venous blood for chemistry and hematology panels and lumbar CSF for routine studies were obtained every other day for one week, and weekly thereafter. The animals were weighed at the same time blood and CSF was collected.

Toxicity of CRM107 Immunotoxins on Human Medulloblastoma-and Glioblastoma-Derived Cell Lines DT or DT-like toxins such as CRM107 inhibit protein synthesis which, in turn, can be measured for an accurate in vitro assessment of the lethal effect of the toxin on cells.

TABLE 3

IC$_{50}$ Values for CRM 107 and Ricin A Chain Immunotoxins

| | Tf-CRM 107 | 454A12-CRM 107 | 454A12-RTA |
|---|---|---|---|
| Medulloblastoma: Established | | | |
| SNB 40 | 3.9 × 10$^{-13}$ | 3.5 × 10$^{-11}$ | 3.3 × 10$^{-11}$ |
| TE 671 | 2.1 × 10$^{-12}$ | 2.6 × 10$^{-11}$ | 2.6 × 10$^{-11}$ |
| Primary | | | |
| SNB 104 | 2.5 × 10$^{-12}$ | nd | nd |
| SNB 105 | 1.1 × 10$^{-10}$ | nd | nd |
| Glioblastoma: | | | |
| SNB 75 | 6.5 × 10$^{-11}$ | 1.2 × 10$^{-10}$ | 1.5 × 10$^{-10}$ |
| SNB 101 | 5.4 × 10$^{-12}$ | 3.8 × 10$^{-11}$ | 3.0 × 10$^{-10}$ |
| U 251 | 2.6 × 10$^{-12}$ | 1.6 × 10$^{-11}$ | 3.6 × 10$^{-11}$ |

TABLE 3-continued

IC$_{50}$ Values for CRM 107 and Ricin A Chain Immunotoxins

| | Tf-CRM 107 | 454A12-CRM 107 | 454A12-RTA |
|---|---|---|---|
| Breast: | | | |
| MCF-7 | 2.3 × 10$^{-11}$ | 1.2 × 10$^{-10}$ | 3.2 × 10$^{-10}$ |
| T47D | 1.1 × 10$^{-12}$ | 1.0 × 10$^{-10}$ | 7.0 × 10$^{-11}$ |
| ZR-75-1 | 1.6 × 10$^{-11}$ | 2.1 × 10$^{-10}$ | 3.6 × 10$^{-10}$ |

Immunotoxins were incubated with the cells for 24 hrs followed by an incubation of 1 hr with $^{14}$C-leucine. Cells were then harvested and concentrations of immunotoxin that inhibit protein synthesis by 50% of control values (IC50) were determined.

TABLE 4

Maximum Tolerated Dose in Guinea Pig CSF

| Toxin | Concentration |
|---|---|
| DT | 3.2 × 10$^{-11}$ M–3.2 × 10$^{-12}$ M |
| CRM 107 | 3.2 × 10$^{-10}$ |
| Tf-CRM 107 | 2 × 10–9 M |

Toxin alone or Tf-CRM conjugate was injected percutaneously into the cisterna magna of strain 2 guinea pigs. The maximum dose permitting survival was determined. No significant weight loss was observed at these doses when compared with control animals.

FIG. 6a shows representative dose-response curves of the Tf-CRM107 conjugate on four medulloblastoma-derived cell lines. A steep dose-response inhibition of protein synthesis by Tf-CRM017 was observed with all the cell lines. Protein synthesis in SNB 40 cells was inhibited by 50% (IC50) by 3.9×10 –13M Tf-CRM107, as shown in Table 3. TE671 cells and the primary medulloblastoma-derived cell line, SNB 40, were also extremely sensitive to Tf-CRM107 (IC50=2.5×10–12M and 2.1×10–12M, respectively). The IC50 of Tf-CRM107 for the other primary medulloblastoma derived cell line, SNB105, was 1.1×10–10M. The receptor specificity of the Tf-CRM107 conjugate was demonstrated by the fact that excess free Tf blocked cell killing by the toxin conjugate.

FIG. 6b shows results of similar experiments using the glioblastoma-derived cell lines. As observed with cells derived from medulloblastoma, Tf-CRM107 exhibited potent killing with all of the glioblastoma cells. The IC50 for SNB 75 was 6.5×10–11M, while for SNB 101 and U251 it was 5.4×10–12M and 2.6×10–12M, respectively. Using a monoclonal antibody against the human TfR, 454A12, linked to CRM107 on two continuous medulloblastoma cell lines and three glioblastoma cell lines showed IC50 levels between 10–11 and 10–10M, whereas, when this same conjugate was assayed on Vero cells, which lack the receptor, the IC50 level was 1×10–8M. The therapeutic window between tumor and nontarget cells is therefore 100 to 1000-fold. These reagents are highly potent and specifically toxic to brain tumor cells.

Comparison of the Toxicity of Anti-transferrin Receptor Antibody Conjugated to Ricin A Chain and to CRM107

The toxicity of the anti-Tfr antibody, 454A12, conjugated to recombinant ricin A chain (RTA) or to CRM1107 was compared with Tf- CRM107 on medulloblastoma- and glioblastoma-derived cell lines, as shown in Table 3. Both 454A12-RTA and 454A12-CRM107 immunotoxin displayed very similar toxicities when evaluated after 24 hours using the in vitro assay of protein synthesis described above. The IC50 observed for both of these immunotoxins on established medulloblastoma and glioblastoma cell lines ranged from approximately 10–10M to 10–11M. Only one cell line, SNB 101, displayed a significant difference in sensitivity to the two immunotoxins. For this cell line, 454A12-CRM107 was approximately 10-fold more toxic than 454A12-RTA.

Three established breast-derived cell lines, MCF-7, T47D, and ZR-75-1, were assayed, since breast tumors are the most common tumor leading to meningeal carcinomatosis, cf. Table 3. These cells displayed approximately the same sensitivity to the immunotoxins as found for the medulloblastoma or glioblastoma cells. In a 24 hour assay, the IC50 was similar for both 454A12-RTA and 454A12-CRM107, ranging from between 1× 10–10M and 7×10–11M. Tf-CRM107 was approximately 10- to 100-fold more toxic than the 454A12 immunotoxins on these breast cell lines.

FIG. 7 demonstrates very different dose response curves for 454A12-CRM107 and 454A12-RTA after three hours of incubation with the immunotoxins on representative cell lines derived from medulloblastoma, glioblastoma, and breast carcinoma. The 454A12-CRM107 displayed a steep dose-response curve on all three cell lines, with an IC50 between 1×10–10M and 6×10–10M. The RTA immunotoxin is less toxic, inhibiting protein synthesis by less that 30% in TE 671 and U251 cells at concentrations greater than 10–7M. 454A12-RTA is approximately 15-fold less toxic to T47D breast carcinoma cells than the CRM 107 immunotoxin.

Similar dose response curves for 454A12-CRM107 and 454A12-RTA were obtained in a 24 hour assay, as shown in Table 3, yet very different curves result from a three hour assay with the two toxin conjugates, as can be seen in FIG. 7. This indicates that large differences exist in the rate of cell killing by the two immunotoxins. Kinetic differences in the rate of killing by immunotoxins can be masked in an assay where inhibition of protein synthesis is measured over a long incubation period. The assay cannot detect cell killing beyond 90% of the input cells (10% of control protein synthesis). Immunotoxins with rapid killing may reach this level quickly and continue to kill additional logs of cells that are not detected in the assay. After long incubation times, the dose-response curves of immunotoxins with efficient killing rates may appear identical to those with less efficient rates of kill, since the assay does not relate the additional log-kill.

Maximum Tolerable Dose In Vivo Guinea Pigs

To investigate the feasibility of intrathecal immunotoxin therapy for tumors in the cerebrospinal fluid, the toxicity of DT, CRM107, and Tf-CRM107 was determined. Varying concentrations of the toxins were injected percutaneously into the cisterna magna of guinea pigs. The maximum safe dose (maximum dose where no significant weight loss was observed) of DT was between 3.2×10–11M to 3.2×10–12M, as shown in Table 4. Up to 100-fold higher doses of CRM107 were tolerated without detectable toxicity. Therefore, in vivo toxicity of CRM107 is about 1/100 of that of DT, while the nonspecific toxicity of CRM107 in vitro is 1/10,000 that of DT. Furthermore, conjugation of CRM107 to Tf reduced the toxicity approximately 10-fold more (2×10–9M). Inactivation of toxicity due to conjugation was previously observed with other immunotoxins.

Rhesus Monkeys

Tf-CRM107 was injected intrathecally into the cisterna magna of adult Rhesus monkeys. Assuming a volume of distribution of 6 cc, doses to produce a CSF concentration of 3.3×10–10M and 2×10–9M were administered. Neither dose of Tf-CRM107 caused apparent neurologic illness, and both animals were alive two months after treatment. Weight loss was limited to less than 10% of baseline. At both doses, prominent fevers (greater than 39.5°) occurred on days one and two following treatment. Serum chemistry, liver enzymes, renal function, and hematologic parameters did not change. A CSF inflammatory response with pleocytosis, elevated protein, and normal glucose was apparent for 48 hours, but had largely-resolved by 14 days after treatment.

The concentration of 2×10–9M which was reached safely in vivo is 20–5000 times greater than the IC50 of Tfn-CRM107 to all the medulloblastoma, glioblastoma, or breast cells assayed in culture.

Inhibiting Effects of Circulating Anti-DT Antibodies

A critical factor in the efficacy of any CRM107 immunotoxin in man is the level of inactivating anti-DT immunoglobulin produced by intentional immunization with diphtheria toxoid. Since CRM107 differs in only one amino acid from DT, it is expected that the majority of circulating antibodies would be cross-reactive with CRM107. The effect of circulating levels of antibody in the serum was investigated, along with the effect of CSF on DT toxicity.

As shown in FIG. 8*a*, most human sera contain significant titers of inactivating antibody. Further titration of the sera with higher level of DT revealed approximately a 10,000-fold block by sera. Two donors, reportedly not intentionally immunized against DT, exhibited dose-response curves that closely parallel the control DT curve, and serve as controls showing the human sera has no other effects on DT toxicity.

Low levels or total absence of inactivating antibody was found in the CSF (FIG. 8*b*) of normal volunteers. CSF from a glioblastoma patient, a patient with breast cancer-related leptomeningeal carcinomatosis, and one patient with lymphomatous leptomeningitis was also tested and showed no inhibition of DT toxicity. The fact that CSF has 0.2% to 0.4% of the IgG found in serum is consistent with the results found. These results substantiate the belief that the CSF compartment is an immunologically privileged site.

Inhibition of Tf-CRM107 and 454A12-CRM107 by Free Tfn.

Cerebrospinal fluid is reported to have 14 micrograms/ml of circulating Tf. The effect of this concentration of free Tf was tested on the toxicity produced by Tf-CRM107. The human erythroblastoma-derived cell line, K562, has been shown to express high levels of TfR (1.5×105 sites per cell), and as a result, is extremely sensitive to the Tf-CRM107 conjugate. Therefore, using K562 cells, free Tf (14 micrograms/ml) was found to inhibit the Tf-CRM107 conjugate four-fold and to have no effect on native DT, as shown in FIG. 9. Therefore, circulating levels of Tf in the cerebrospinal fluid are sufficient to cause only a very minor block of toxicity.

Binding of 454A12-RTA and 454A12-CRM107 was mediated by the antibody portion of the conjugate as shown by the fact that free antibody could block toxicity. Binding of 454A12 to the TfR is not inhibited by free Tf; Tf, at 14 micrograms/ml concentrations found in the cerebrospinal fluid, had no effect on the toxicity of either 454A12 immunotoxin.

CRM107 can be used for the construction of highly potent immunotoxins directed specifically at tumors of the central nervous system. Immunotoxins may be most effective for the regional treatment of disease confined to an anatomic compartment where transvascular delivery is not a problem and where relatively high local concentrations, and therefore greater therapeutic effect, may be achieved. It was previously shown that an anti-idiotype monoclonal antibody-ricin immunotoxin, delivered intrathecally, significantly extended survival in a guinea pig model of leptominingeal neoplasia. The increased survival, which corresponded to a median 2–3 log kill of tumor cells, occurred without detectable toxicity related to the immunotoxin.

Of the immunotoxins described above, CRM107 represents a significant advance in the design of toxins for use in immunotoxin therapy. CRM107 is a genetically modified form of DT, differing from native DT at amino acid position 525. The toxin molecule consists of an A and B subunit. The A subunit enzymatically inactivates protein synthesis by transferring ADP ribose to elongation factor 2, thereby stopping the addition of amino acids to the growing polypeptide chain and thus killing the cell. The B subunit has two functions, facilitating both the binding of the toxin to the cell surface and the entry or translocation of the A subunit across the cell membrane into the cytosol where it functions. The advantage of CRM107 is that the amino acid change in the toxin B chain inactivate toxin binding 8000-fold, yet has no effect on the translocation function. Therefore, by linking CRM107 to a specific binding moiety such as a tumor-specific monoclonal antibody, it is possible to target the full toxicity of the native toxin yet avoid the problems of non-specific toxicity caused by toxin binding.

The advantages of CRM107-based immunotoxins become apparent when compared with immunotoxins made with DT A chains alone. Colombatti et al., reported in *J Diol Chem* 261: 3030–3035 , 1986, compared the toxicity of native DT conjugated with a monoclonal antibody specific for the T lymphocyte antigen receptor with that of the DT A chain conjugated to the same antibody. A chain immunotoxins were found to be 10,000-fold less toxic than those made with native DT. This reduction in toxicity reflects the loss of the B chain translocation function. CRM107 retains the translocation function, and therefore, when linked to a new binding site, maintains the full potency of killing found in the native toxin but with the high cell-type specificity of A chain conjugates.

Medulloblastoma-, gliblastoma-, and breast carcinoma-derived cell lines were used to assess the in vitro efficacy of CRM107-based immunotoxins for treatment of tumors of the cerebrospinal fluid compartment. These three types of tumors were selected because they represent examples of central nervous system tumors which frequently cause morbidity and mortality by leptomeningeal involvement and which are often difficult to treat with conventional forms of therapy. The in vitro results described above indicate that immunotoxin therapy offers certain advantages over existing treatments of these tumors.

Medulloblastoma comprises 20% of all brain tumors in children. Because of the high incidence of recurrence and the propensity for dissemination through the cerebrospinal fluid, these children require postoperative radiation therapy which usually impairs their intellectural and physical development. A more targeted treatment such as immunotoxin therapy would be especially useful for this type of tumor. Intrathecal immunotoxin treatment of medulloblastoma has the added advantage of free access to the tumor cells within the cerebrospinal fluid, avoiding the potential problem of limited penetration into the tumor mass.

Glioblastoma, the most common primary malignant brain tumor, is rapidly fatal. The best treatment currently available, utilizing surgery, radiation therapy, and systemic chemotherapy, results in median survival times of less than one year. Inasmuch as most treatment failures occur because of local recurrence of glioma, immunotoxins administered directly into the cerebrospinal fluid or tumor, avoiding delivery problems caused by the blood-brain barrier, provide additional tumor response and enhanced log-kill required for effective treatment of gloiblastoma.

A variety of carcinomas, most commonly breast, metastasize to the leptomeninges. The incidence of meningeal carcinomatosis in breast cancer is believed to be rising because of improvements in the management of systemic disease. Diffuse secondary involvement of the leptomeninges without focal parenchymal involvement is occasionally reported. These patients are particularly suited for immunotoxin therapy since the problems involved with penetration of a solid tumor mass by immunotoxins are minimal.

The above-described experiments compared the efficacy of immunotoxins made with CRM107 and RTA on representative cell lines derived from medulloblastoma, glioblastoma, and breast carcinoma. A monoclonal antibody to TfR, 454A12, was linked to each toxin and the in vitro toxicity was examined. Using a 24-hour inhibition of protein synthesis assay, both immunotoxins killed these cell lines at concentrations ranging from 10–10 and 10–11M. However, it was found the CRM107 immunotoxins kill at a much faster rate than the RTA immunotoxins. A shorter incubation time, e.g. three hours, for the in vitro assay demonstrates these kinetic differences. In these assays, 454A12-CRM107 is 10 to 1000-fold more toxic than 454A12-RTA. The CRM107 conjugates displayed steep dose response curves, again indicative of rapid killing. This increase in the rate of killing of CRM107 immunotoxins compared to those made with RTA probably reflects the potentiating effect derived form the B chain entry function.

Immunotoxins made with antibodies and whole toxins that are genetically altered in their binding domain possess several advantages over antibody-toxin A-chain conjugates. First, as shown with diphtheria toxin, the B-chain translocation activity can be used in the absence of its binding function to increase reagent potency 10,000-fold over that of A-chain conjugates. Reduction of the disulfide linkage leads to rapid ross of immunotoxin in vivo, and the release of free antibody that can bind more cells and compete with intact immunotoxins. Use of whole toxins permits construction of noncleavable thioether linkages between toxin and antibody. Intact toxins are less susceptible to proteolytic inactivation than are toxin A fragments, and may survive longer in vivo.

The immunotoxins of the present invention have full A-chain activity and full B-chain translocation activity, but they lack the binding for native diphtheria toxin and possess a new binding domain, which is covalently attached. The immunotoxins of the present invention have a greater potency than any previously proposed immunotoxin, and have greater selectivity between antigen positive and antigen negative cells.

Conjugates of the binding moiety and the inactivated diphtheria toxin may be made using a variety of bifunctional protein coupling agents. Examples of such reagents are SPDP, iminothiolane (IT), bifunctional derivatives of imidoesters such as dimethyl adipimidate HCl, active ester such as disuccinimidyl suberate, aldehydes such as glutaraldehyde, bis-azido compound such as bis(p-azidobenzoyl) hexanediamine, bis-diazonium derivatives such as bis-(p-diazoniumbenzoyl)ethylenediamine, diisocyanates such as tolylene 2,6-diisocyanate, and bis-active fluorine compounds such as 1,5-difluoro-2,4-dinitrobenzene. The binding moiety, if it contains a carbohydrate moiety, may be linked to the diphtheria toxin by means of a covalent bond to an oxidized carbohydrate moiety on the antibody as disclosed by U.S. Pat. No. 4,671,958 incorporated herein by reference.

The immunotoxins of the present invention are useful in the treatment of any condition requiring bone marrow transplantation. That is, T-cell activity from peripheral blood which contaminates human bone marrow transplants can be largely eliminated by prior treatment with the immunotoxins of the present invention by preventing the reaction of T-cells in the donor marrow against the host cells, causing graft-versus-host disease. Therefore, this reagent is particularly useful in the treatment of aplastic anemia or leukemia patients who receive bone marrow transplants.

In treating such conditions, human bone marrow and peripheral blood mononuclear cells are treated with varying concentrations of an immunotoxin prepared according to the present invention. The T-lymphocyte cell activity can be reduced by the immunotoxins at concentrations which have very little effect on the activity of the stem cells necessary to repopulate the patient's marrow.

The protocol used for the actual treatment of human donor bone marrow is as follows: The bone marrow is removed from the human donor, treated in vitro with an immunotoxin according to the present invention, and then infused into the irradiated recipient.

It is logical that an immunotoxin which kills at a faster rate will ultimately produce greater log kill than a slower acting immunotoxin. Laurent et al., in *Cancer Res* 46: 2289–2294, 1986, demonstrated this principle using a clonogenic assay. It was found that immunotoxins with the fastest kinetics of killing also exhibited the greatest log kill of human lymphocytes. It would thus be expected that the in vivo efficacy of CRM107 immunotoxins would surpass that of RTA immunotoxins.

Tf, unlike many monoclonal antibodies, cross-reacts among species. Therefore, by linking Tf with CRM107, it was possible to evaluate the toxicity of the conjugate administered intrathecally in both guinea pigs and rhesus monkeys. Problems encountered in the periphery which would limit the efficacy of Tf-CRM107, i.e., high levels of Tf and circulating anti-DT antibodies, do not appear to occur in the CSF. In rhesus monkeys, the highest dose of Tf-CRM 107 tested (2×10–9M) was without toxicity. In guinea pigs, the maximum tolerated dose in the cerebrospinal fluid was 2×10–9M. The concentration of Tf-CRM107 required to kill 50% of the cells derived from medulloblastoma, glioblastoma, or breast carcinoma in vitro ranged from 1×10–10M to 4×10–13M. Therefore, it was possible to achieve a concentration of the conjugate in the cerebrospinal fluid that is from 20- to 5000-fold higher than that effective in vitro without detectable animal toxicity.

The CRM107 conjugates of the present invention represent a significant advance in immunotoxin efficacy. They combine a high degree of tumor specificity, the ultimate degree of potency (one molecule per cell is sufficient to kill), with extremely rapid killing to produce a therapeutic window of up to 5000-fold. These factors, together with the advantages offered by compartmentalized treatment, demonstrate that CRM107 immunotoxins have considerable potential for the treatment of leptomeningeal neoplasia.

The foregoing description of the specific embodiments will so fully reveal the general nature of the invention that other can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A toxin conjugate comprising (i) a mutant diphtheria toxin, wherein said mutant diphtheria toxin has a cell surface receptor binding site that binds to said cell surface receptor with an affinity lower than that of wild-type diphtheria toxin and a translocation function, and has an amino acid point mutation of serine residue 508 or of serine residue 525, covalently attached to (ii) a binding moiety which binds to a specific receptor;

wherein said translocation function is measured by a cytotoxicity assay using said conjugate and a cell expressing said specific receptor.

2. A toxin conjugate according to claim 1, wherein said mutant diphtheria toxin has a serine to phenylalanine mutation at residue 508.

3. A toxin conjugate according to claim 1, wherein said mutant diphtheria toxin has a serine to phenylalanine mutation at residue 525.

4. A toxin conjugate according to claim 1, wherein said binding moiety is transferrin.

5. A toxin conjugate according to claim 1, wherein said binding moiety is a monoclonal antibody which specifically binds to the T3 antigen receptor on human T-cells.

6. A toxin conjugate according to claim 1, wherein said binding moiety is epidermal growth factor.

7. A toxin conjugate according to claim 1, wherein said binding moiety is a monoclonal antibody that specifically binds to transferrin receptor.

8. A method for the treatment of graft versus host disease which comprises:

i) obtaining bone marrow cells from a donor;

ii) incubating said bone marrow cells with an immunotoxin according to claim 1; and iii) injecting said bone marrow cells treated in step (ii) into an irradiated recipient.

9. The method of claim 8, wherein said binding moiety is transferrin or a monoclonal antibody that specifically binds to a transferrin receptor.

10. A method for selectively removing T cells from a sample of bone marrow cells which comprises incubating said bone marrow cells with an immunotoxin according to claim 1.

11. A method according to claim 10, wherein the binding moiety of said immunotoxin is a monoclonal antibody.

12. The method of claim 11, wherein said monoclonal antibody is a monoclonal antibody which specifically binds to the T3 antigen receptor on human T-cells.

13. A method for selectively killing leukemia cells, which comprises contacting said leukemia cells with an immunotoxin according to claim 1, wherein the binding moiety of said immunotoxin is a monoclonal antibody which specifically binds to the T3 antigen receptor on human T-cells.

14. The method of claim 13, wherein said mutant diphtheria toxin contains a point mutation of serine residue 508 to phenylalanine or a mutation of serine residue 525 to phenylalanine.

15. A toxin conjugate according to claim 1, wherein said mnutant diphtheria toxin has an amino acid point mutation of serine residue 508.

16. A toxin conjugate according to claim 1, wherein said mutant diphtheria toxin has an amino acid point mutation of serine residue 525.

17. A toxin conjugate according to claim 1, wherein said specific receptor is resident on the surface of a target cell.

18. A method for enhancing the selectivity of a mutant diphtheria toxin which comprises covalently attaching (i) a mutant diphtheria toxin, wherein said mutant diphtheria toxin has a cell surface receptor binding site that binds to said cell surface receptor with an affinity lower than that of wild-type diphtheria toxin and a translocation function, and having an amino acid point mutation of serine residue 508, or an amino acid point mutation of serine residue 525, to (ii) a binding moiety which binds to a specific receptor;

wherein said translocation function is measured by a cytotoxicity assay using said conjugate and a cell expressing said specific receptor.

19. The method according to claim 18, wherein said binding moiety is selected from the group consisting of transferrin, a monoclonal antibody and epidermal growth factor.

20. The method of claim 19, wherein the binding moiety is transferrin.

21. The method of claim 19, wherein the binding moiety is a monoclonal antibody which specifically binds to transferrin receptor.

22. The method of claim 19, wherein the binding moiety is epidermal growth factor.

23. The method of claim 19, wherein the binding moiety is a monoclonal antibody which specifically binds to the T3 antigen receptor on human T-cells.

24. A method according to claim 18, wherein said specific receptor is resident on the surface of a target cell.

25. A toxin conjugate comprising (i) a binding moiety which specifically binds to a receptor of a cell of a neural cell tumor, a glial cell tumor, a metastatic small cell lung carcinoma or metastatic breast carcinoma tumor and (ii) a mutant diphtheria toxin, wherein said mutant diphtheria toxin consists of an A chain polypeptide and a B chain polypeptide, wherein said B chain polypeptide has a cell surface receptor binding site that binds to said cell surface receptor with a binding affinity lower than that of wild-type diphtheria toxin and an A chain translocating activity, and wherein said B chain has an amino acid point mutation of serine residue 508 or of serine residue 525, wherein said binding moiety is covalently linked to said mutant diphtheria toxin;

wherein said A chain translocating activity is measured by a cytotoxicity assay using said conjugate and a cell expressing said specific receptor.

26. A toxin conjugate of claim 25, wherein said cell is a glioblastoma or medulloblastoma cell.

27. A toxin conjugate of claim 25, wherein said mutant diphtheria toxin has a point mutation of serine residue 508 to phenylalanine or of serine residue 525 to phenylalanine.

28. A toxin conjugate of claim 25, wherein said receptor is a transferrin receptor.

29. A toxin conjugate of claim 28, wherein said binding moiety is transferrin or a monoclonal antibody which specifically binds to a transferrin receptor.

30. A toxin conjugate according to claim 25, wherein said specific receptor is resident on the surface of a target cell.

31. A toxin conjugate comprising (i) a mutant diphtheria toxin, wherein said mutant diphtheria toxin has a cell surface receptor binding site that binds to said cell surface receptor with an affinity lower than that of wild-type diphtheria toxin and has a point mutation of serine residue 508 and a point mutation of proline residue 308, covalently attached to (ii) a binding moiety which binds to a specific receptor.

32. A toxin conjugate according to claim 31, wherein said mutations of serine residue 508 and of proline residue 308 change said serine residue 508 to phenylalanine and change said proline residue 308 to serine.

33. A toxin conjugate according to claim 31, wherein said binding moiety specifically binds to the T3 receptor on human T cells.

34. A method for selectively removing T cells from a sample of bone marrow which comprises incubating said bone marrow cells with an immunotoxin according to claim 31.

35. A toxin conjugate according to claim 31, wherein said binding moiety is one that specifically binds to the transferrin receptor.

36. A method for selectively killing leukemia cells, which comprises contacting said leukemia cells with an immunotoxin according to claim 33.

37. A toxin conjugate according to claim 33, wherein said binding moiety is a monoclonal antibody that specifically binds to the T3 antigen of T cells.

38. A toxin conjugate comprising (i) a mutant diphtheria toxin, wherein said mutant diphtheria toxin consists of an A chain polypeptide and a B chain polypeptide, wherein said B chain polypeptide has a cell surface receptor binding site that binds to said cell surface receptor with a binding affinity lower than that of wild-type diphtheria toxin and has a point mutation of serine residue 508 and a point mutation of proline residue 308, covalently attached to (ii) a binding moiety which specifically binds to a receptor of a cell of a neural cell tumor, a glial cell tumor, a metastatic small cell lung carcinoma or a metastatic breast carcinoma tumor.

39. A toxin conjugate according to claim 38, wherein said mutations of serine residue 508 and of proline residue 308 change said serine residue 508 to phenylalanine and change said proline residue 308 to serine.

* * * * *

UNITED STATES PATENT AND TRADEMARK OFFICE

CERTIFICATE OF CORRECTION

PATENT NO. : 5,792,458 
DATED : August 11, 1998
INVENTOR(S) : Virginia G. Johnson, Larry Greenfield, Richard J. Youle, and Walter Laird It is certified that error appears in the above-identified patent and that said Letters Patent is hereby corrected as shown below:

Column 1,
Line 49, change “in vitro” to -- *in vitro* --.
Line 50, change “in vitro” to -- *in vitro* --.

Column 2,
Line 42, change “in vitro” to -- *in vitro* --.

Column 3,
Line 23, change “in vitro” to -- *in vitro* --.
Line 29, change “in vitro” to -- *in vitro* --.
Line 32, change “in vivo” to -- *in vivo* --.

Column 4,
Line 20, change “in vitro” to -- *in vitro* --.
Line 29, change “UCHTI” to -- UCHT1 --.
Line 29, change “UCHTI” to -- UCHT1 --.

Column 5,
Line 29, change “UCHTI” to -- UCHT1 --.

Column 6,
Line 48, change “DBR322 to -- pBR322 --.

Column 7,
Line 7, change “2 ´ $10^{-9}$” to -- 2 ´ $10^{-9}$M --.

Column 8,
Line 16, change “tox gene” to -- toxin gene --.
Line 62, change “UCHTI” to -- UCHT1 --.

Column 9,
Line 32, change “Lumber” to -- number --.

Column 10,
Lines 32, 41, 42, 53, 60, 60, and 61, change “UCHTI” to -- UCHT1 --.
Line 61, change “UCHTI” to -- UCHT1 --.
Line 64, change “UCHTI” to -- UCHT1 --.
Line 67, change “UCHTI” to -- UCHT1 --.

UNITED STATES PATENT AND TRADEMARK OFFICE
CERTIFICATE OF CORRECTION

PATENT NO. : 5,792,458
DATED : August 11, 1998
INVENTOR(S) : Virginia G. Johnson, Larry Greenfield, Richard J. Youle, and Walter Laird It is certified that error appears in the above-identified patent and that said Letters Patent is hereby corrected as shown below:

Column 11,
Line 1, change "UCHTI" to -- UCHT1 --.
Lines 6, 9, and 16, change "UCHTl" to -- UCHT1 --.
Line 40, change "Wehl" to -- Wehi --.
Line 47, change "Limtations" to -- Limitation --.

Column 12,
Line 14, change "UCHTl" to -- UCHT1 --.

Column 14,
Line 1, change "PH 8.5" to -- pH 8.5 --.

Column 16,
Line 10, change "3.6 ´ $10^{-10}$" to -- 3.8 ´ $10^{-10}$ --.
Line 63, change "CRM1107" to -- CMR107 --.

Column 21,
Line 46, change "Tf-CRM 107" to -- Tf-CRM107 --.

Column 22,
Line 63, change "mnutant" to -- mutant --.

Signed and Sealed this

Twenty-seventh Day of November, 2001

Attest:

NICHOLAS P. GODICI
*Attesting Officer*  *Acting Director of the United States Patent and Trademark Office*